United States Patent
Kitagawa et al.

(10) Patent No.: US 8,630,447 B2
(45) Date of Patent: Jan. 14, 2014

(54) ANALYZER OF ULTRASONIC FLAW DETECTION IMAGE

(75) Inventors: Tomoaki Kitagawa, Takasago (JP); Hiroshi Takemoto, Nagoya (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 123 days.

(21) Appl. No.: 13/146,991

(22) PCT Filed: Feb. 23, 2010

(86) PCT No.: PCT/JP2010/052773
§ 371 (c)(1),
(2), (4) Date: Sep. 9, 2011

(87) PCT Pub. No.: WO2010/098325
PCT Pub. Date: Sep. 2, 2010

(65) Prior Publication Data
US 2011/0311097 A1    Dec. 22, 2011

(30) Foreign Application Priority Data
Feb. 26, 2009   (JP) ................................. 2009-043475

(51) Int. Cl.
*G06K 9/00*   (2006.01)
(52) U.S. Cl.
USPC ........................................................ 382/100
(58) Field of Classification Search
None
See application file for complete search history.

(56) References Cited

U.S. PATENT DOCUMENTS 8,100,014 B2 *  1/2012  Fukutomi et al. ............... 73/598
2006/0265094 A1   11/2006  Numata

FOREIGN PATENT DOCUMENTS

| JP | 4-352954 | 12/1992 |
|---|---|---|
| JP | 09-251364 | 9/1997 |
| JP | 2001-143005 | 5/2001 |
| JP | 2001-224591 | 8/2001 |
| JP | 2003-050630 | 2/2003 |
| JP | 2006-189422 | 7/2006 |
| JP | 2007-232462 | 9/2007 |

OTHER PUBLICATIONS

International Search Report issued Mar. 30, 2010 in International (PCT) Application No. PCT/JP2010/052773.
Written Opinion of the International Searching Authority issued Mar. 30, 2010 in International (PCT) Application No. PCT/JP2010/052773.

* cited by examiner

*Primary Examiner* — Nirav G Patel
(74) *Attorney, Agent, or Firm* — Wenderoth, Lind & Ponack, L.L.P.

(57) ABSTRACT

A flaw detection image analyzer (10) takes in an inspection procedure command stored in a flaw detection condition database (40), takes in a flaw detection image signal corresponding to a flaw detection image indicated by the taken inspection procedure command from a database (50) for flaw detection image signal, and displays the flaw detection image based on the flaw detection image signal on a display (30), with a display range and a contrast indicated by the inspection procedure command in an arrangement pattern of image indicated by the inspection procedure command. Consequently, optimum images can be displayed sequentially with optimum arrangement pattern, optimum display range and contrast according to a flaw to be inspected when a flaw is detected by observing an ultrasonic flaw detection image.

1 Claim, 15 Drawing Sheets

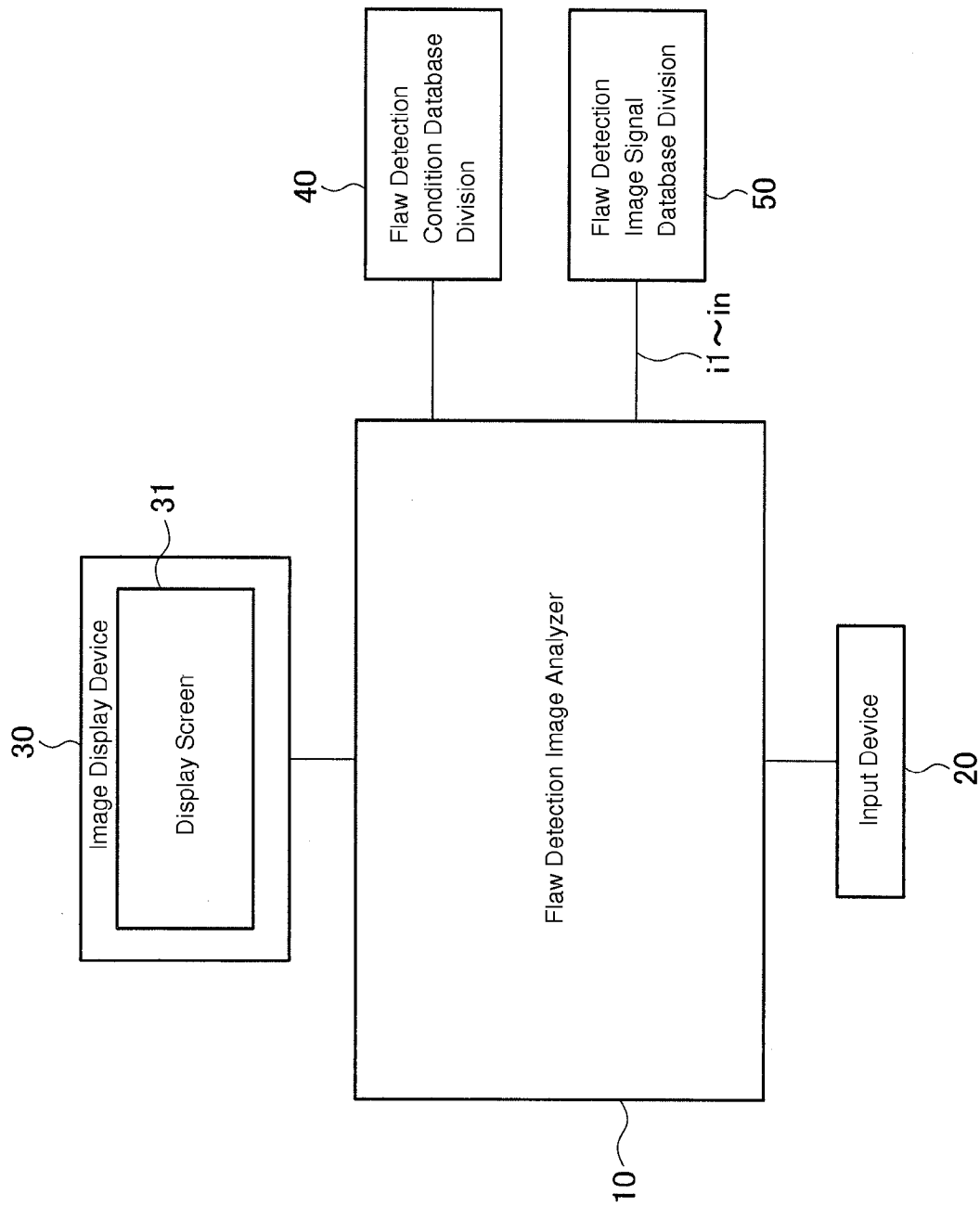

Fig.2

| Inspection procedure command C | Type of defect | Flaw detection image used | Arrangement pattern of image | Display range | | | | Contrast indicated values | |
|---|---|---|---|---|---|---|---|---|---|
| | | | | X1 | X2 | Y1 | X2 | Min | Max |
| C1 | D1 | I1 | Maximum enlargement of one image on screen | 0 | 10 | 0 | 20 | 20 | 40 |
| C2 | D1 | I1 | Maximum enlargement of one image on screen | 10 | 20 | 0 | 20 | 20 | 40 |
| C3 | D1 | I1 | Maximum enlargement of one image on screen | 30 | 40 | 0 | 20 | 20 | 40 |
| C4 | D1 | I1 | Maximum enlargement of one image on screen | 50 | 60 | 0 | 20 | 20 | 40 |
| ⋮ | ⋮ | ⋮ | ⋮ | ⋮ | ⋮ | ⋮ | ⋮ | ⋮ | ⋮ |
| C101 | D2 | I1 | Laterally aligned arrangement | 0 | 10 | 0 | 20 | 20 | 40 |
| | | I4 | | 0 | 10 | 0 | 20 | 30 | 50 |
| C102 | D2 | I1 | Laterally aligned arrangement | 10 | 20 | 0 | 20 | 20 | 40 |
| | | I4 | | 10 | 20 | 0 | 20 | 30 | 50 |
| C103 | D2 | I1 | Laterally aligned arrangement | 20 | 30 | 0 | 20 | 20 | 40 |
| | | I4 | | 20 | 30 | 0 | 20 | 30 | 50 |
| ⋮ | ⋮ | ⋮ | ⋮ | ⋮ | ⋮ | ⋮ | ⋮ | ⋮ | ⋮ |
| CN | D3 | I2 | Laterally aligned arrangement | 0 | 10 | 0 | 20 | 10 | 50 |
| | | I3 | | 0 | 10 | 0 | 20 | 20 | 30 |
| N+1 | D3 | I2 | Laterally aligned arrangement | 10 | 20 | 0 | 20 | 10 | 50 |
| | | I3 | | 10 | 20 | 0 | 20 | 20 | 30 |
| N+2 | D3 | I2 | Laterally aligned arrangement | 30 | 40 | 0 | 20 | 10 | 50 |
| | | I3 | | 30 | 40 | 0 | 20 | 20 | 30 |
| ⋮ | ⋮ | ⋮ | ⋮ | ⋮ | ⋮ | ⋮ | ⋮ | ⋮ | ⋮ |

| Inspection procedure command C | Type of defect | Display range | | | | Plate thickness | Shape | Material |
|---|---|---|---|---|---|---|---|---|
| | | X1 | X2 | Y1 | X2 | | | |
| C1 | D1 | 0 | 10 | 0 | 20 | 10 | F1 | M1 |
| C2 | D1 | 10 | 20 | 0 | 20 | 15 | F1 | M1 |
| C3 | D1 | 20 | 30 | 0 | 20 | 20 | F1 | M1 |
| C4 | D1 | 30 | 40 | 0 | 20 | 10 | F1 | M1 |
| ⋮ | ⋮ | ⋮ | ⋮ | ⋮ | ⋮ | ⋮ | ⋮ | ⋮ |
| C101 | D2 | 0 | 10 | 0 | 20 | 10 | F2 | M2 |
| C102 | D2 | 10 | 20 | 0 | 20 | 15 | F2 | M2 |
| C103 | D2 | 20 | 30 | 0 | 20 | 15 | F2 | M2 |
| ⋮ | ⋮ | ⋮ | ⋮ | ⋮ | ⋮ | ⋮ | ⋮ | ⋮ |
| CN | D3 | 0 | 10 | 0 | 20 | 10 | F3 | M3 |
| N+1 | D3 | 10 | 20 | 0 | 20 | 20 | F3 | M3 |
| N+2 | D3 | 20 | 30 | 0 | 20 | 10 | F3 | M3 |
| ⋮ | ⋮ | ⋮ | ⋮ | ⋮ | ⋮ | ⋮ | ⋮ | ⋮ |

| Type of defect | Plate thickness | Shape | Material | Flaw detection image used | Arrangement pattern of image | Contrast indicated values | |
|---|---|---|---|---|---|---|---|
| | | | | | | Min | Max |
| D1 | 10 | F1 | M1 | I1 | Maximum enlargement of one image on screen | 20 | 40 |
| | 15 | F1 | M1 | I1 | Maximum enlargement of one image on screen | 20 | 40 |
| | 20 | F1 | M1 | I1 | Maximum enlargement of one image on screen | 20 | 40 |
| D2 | 10 | F2 | M2 | I1 | Laterally aligned arrangement | 20 | 40 |
| | | | | I3 | | 30 | 50 |
| | 15 | F2 | M2 | I1 | Laterally aligned arrangement | 20 | 40 |
| | | | | I3 | | 30 | 50 |
| | 20 | F2 | M2 | I1 | Laterally aligned arrangement | 20 | 40 |
| | | | | I3 | | 30 | 50 |
| D3 | 10 | F3 | M3 | I2 | Laterally aligned arrangement | 10 | 20 |
| | | | | I4 | | 30 | 40 |
| | 15 | F3 | M3 | I2 | Laterally aligned arrangement | 10 | 20 |
| | | | | I4 | | 30 | 40 |
| | 20 | F3 | M3 | I2 | Laterally aligned arrangement | 10 | 20 |
| | | | | I4 | | 30 | 40 |
| ⋮ | ⋮ | ⋮ | ⋮ | ⋮ | ⋮ | ⋮ | ⋮ |

ANALYZER OF ULTRASONIC FLAW DETECTION IMAGE

TECHNICAL FIELD

This invention relates to an analyzer or analytical apparatus for an ultrasonic flaw detection image, which is designed to be capable of reducing labor and time for conducting an inspection for a defect and also capable of detecting the defect accurately regardless of the degree of mastery.

BACKGROUND ART

The main wing of an aircraft has so far been produced using an aluminum alloy or a titanium alloy, but recently, has used a carbon fiber-reinforced plastic (CFRP) comprising a combination of carbon fibers and resin.

In the aircraft, damage to the wing poses a danger directly leading to a serious accident. Thus, it is very important to perform operations for maintenance and checkup, thereby finding a defect.

Defects occurring in the wing of the aircraft include a flaw, foreign matter, a peel, and so on. As a nondestructive examination for detecting these defects, an ultrasonic flaw detection test or inspection is adopted.

A general technique for the ultrasonic flaw detection test will be explained first of all.

If a flaw detection range A is broad, as shown in FIG. 10, a flaw detection path P is established or set. Along this flaw detection path P, an ultrasonic probe is moved to acquire a flaw detection waveform signal (response waveform signal) by an ultrasonic wave.

If, at a certain point on the flaw detection path P, this site is a sound site, a flaw detection waveform signal, which comprises a surface echo $E_s$ and a bottom echo $E_b$ as shown in FIG. 11, is obtained. If, at a certain point on the flaw detection path P, this site is a defective site, a flaw detection waveform signal, which comprises the surface echo $E_s$, the bottom echo $E_b$, and a defect echo $E_d$ as shown in FIG. 12, is obtained.

If the flaw detection range A is narrow, it is possible to detect a defect (detect the defect echo $E_d$) by visually observing the waveform of the flaw detection waveform signal throughout the flaw detection path P. If the flaw detection range A is wide, on the other hand, the visual confirmation of the waveform of the flaw detection waveform signal over the entire flaw detection path P takes a huge time.

Under these circumstances, the flaw detection waveform signal is subjected to signal transformation or signal conversion to convert this signal into a flaw detection image signal representing a flaw detection image in which the luminance or brightness value of the defective site changes relative to the brightness value of the sound site. By visually confirming the flaw detection image based on this flaw detection image signal to determine whether there is a defect or not, a flaw detection examination or test is conducted in a short time.

If the presence of the defect is observed, a detailed analysis can be made by confirming the flaw detection waveform which is the basis for the flaw detection image.

As techniques for signal transformation for converting the flaw detection waveform signal into the flaw detection image signal, TOF image signal transformation and AMP image signal transformation are known.

To carry out signal transformation, a gate G with a predetermined range and at a predetermined height is set at a position between the surface echo $E_s$ and the bottom echo $E_b$ in each of FIG. 13 showing the flaw detection waveform signal on the sound site and FIG. 14 showing the flaw detection waveform signal on the defective site.

For conversion into a TOF image, the position where the set gate G and the defect echo $E_d$ intersect is converted into a brightness value. For conversion into an AMP image, the height of the defect echo $E_d$ intersecting the set gate G is converted into a brightness value.

If a plurality of the defect echoes are present, there are versions, for example, in which the first echo that intersects the gate G is used as the defect echo $E_d$, or the highest echo of the echoes intersecting the gate G is used as the defect echo $E_d$.

FIG. 15 shows an example of the flaw detection image of the sound site. FIG. 16 shows an example of the flaw detection image (TOF image) of the defective site. FIG. 17 shows an example of the flaw detection image (AMP image) of the defective site.

As shown in these drawings, the flaw detection image shows the brightness of the defective site changing relative to the brightness of the sound site, and enables the defective site to be inspected visually with rapidity and ease.

The waveform shape of the flaw detection waveform signal and the status of occurrence of a noise differ according to the type of a defect or the plate thickness, shape, and material of the flaw detection site. Thus, a single flaw detection image may be insufficient to determine accurately whether there is a defect or not.

Thus, a plurality of gates different in position or height are set, in accordance with the type of the defect or the plate thickness, shape, and material of the flaw detection site, to generate a plurality of flaw detection image signals, and a plurality of flaw detection images by the plurality of flaw detection image signals are visually confirmed, whereby the presence or absence of the defect is determined overall.

That is, one flaw detection waveform signal obtained when the probe is moved along the flaw detection path P is subjected to signal transformation by a plurality of different signal transformation techniques to obtain a plurality of flaw detection image signals, and flaw detection images by these plural flaw detection image signals are used to judge globally whether the defect is present or not.

Conversion of a flaw detection waveform signal into a TOF flaw detection image signal, and conversion of a flaw detection waveform signal into an AMP flaw detection image signal are different techniques for signal transformation. Moreover, the conversion of a flaw detection waveform signal into a TOF flaw detection image signal, with the gate G differing, is also a different technique for signal transformation. Furthermore, the conversion of a flaw detection waveform signal into an AMP flaw detection image signal, with the gate G differing, is also a different technique for signal transformation. In these senses, these methods are called "a plurality of different signal transformation techniques".

A general example of globally judging the presence or absence of the defect by the flaw detection images by the plurality of flaw detection image signals obtained by the signal transformation of the one flaw detection waveform signal will be described below.

If the types of the defect are two types, D1 and D2, the plate thickness of the flaw detection site is 10 mm, the materials of the flaw detection site are of two types, M1 and M2, and the shape of the flaw detection site is of two types, F1 and F2, for example, a flaw detection image I1 by a TOF flaw detection image signal obtained by signal transformation of the flaw detection waveform signal with a first gate being set, a flaw detection image I2 by a TOF flaw detection image signal obtained by signal transformation of the flaw detection waveform signal with a second gate being set, a flaw detection image I3 by an AMP flaw detection image signal obtained by signal transformation of the flaw detection waveform signal with a third gate being set, and a flaw detection image I4 by an AMP flaw detection image signal obtained by signal transformation of the flaw detection waveform signal with a fourth gate being set can be used for defect evaluation.

If the allocation of the flaw detection images I1 to I4 is made as in Table 1, the flaw detection images I1 to I4 are visually confirmed in sequence, whereby all the defects can be evaluated.

TABLE 1

Example of allocation for defect evaluation by flaw detection images

| Type of defect | Plate thickness of flaw detection site | Material of flaw detection site | Shape of flaw detection site | Flaw detection image |
|---|---|---|---|---|
| D1 | 10 | M1 | F1 | I1 |
| D1 | 10 | M1 | F2 | I1 |
| D1 | 10 | M2 | F1 | I2, I3 |
| D1 | 10 | M2 | F2 | I4 |
| D2 | 10 | M1 | F1 | I1 |
| D2 | 10 | M1 | F2 | I2 |
| D2 | 10 | M2 | F1 | I1 |
| D2 | 10 | M2 | F2 | I2, I4 |

A conventional technique for conducting the ultrasonic flaw detection test of the main wing of an aircraft will be explained.

With the test of the main wing of the aircraft, the whole surface of the main wing is ultrasonically tested for flaw detection. However, it takes too much time to analyze all of flaw detection waveforms by a flaw detection waveform signal obtained by this test. Thus, the acquired flaw detection waveform signal is subjected to signal transformation by a plurality of different signal transformation techniques to be converted into a plurality of flaw detection image signals. On a plurality of flaw detection images by the plurality of flaw detection image signals, a defective site is identified visually.

On the flaw detection image, the brightness value of the defective site is increased (or decreased) compared with a sound site. By visually confirming a change in brightness between the sound site and the defective site, therefore, the defective site is identified.

In this case, the type and arrangement of the flaw detection image to be visually confirmed differ according to the type of the defect to be detected, or the difference of the site (shape, plate thickness, material). Moreover, the display magnification and contrast of the flaw detection image in which the defect is easy to detect are also different. This is because a manner of reflection of an ultrasonic wave differs according to the type of the defect or the plate thickness, shape or material of each site.

Thus, an inspector repeatedly changes the type and arrangement, display range (magnification) and contrast of the flaw detection image displayed, according to the type of the defect and the difference of the site, and detects the defect by so doing.

The details of such a conventional inspection technique will be described by reference to FIG. 18 which is a flowchart, and FIGS. 19 to 21 showing flaw detection waveform images displayed on the display screen of an image display device.

Assume that a plurality of flaw detection image signals created by signal transformation of a flaw detection waveform signal, which was obtained by the ultrasonic flaw detection test of the main wing of an aircraft, by a plurality of different signal transformation techniques have been previously stored on a flaw detection image signal database.

In starting visual inspection work (Step S1 in FIG. 18), an operator opens a plurality of flaw detection images I1 to In derived from a plurality of flaw detection image signals (Step S2).

Then, the type of a defect to be evaluated (for example, the defect D1 of the first type) is determined (Step S3).

What type of defect should be investigated is judged based on knowledge possessed by the operator (knowledge of the structure, shape, plate thickness and material of the wing, knowledge of the characteristics of the ultrasonic flaw detection test, knowledge acquired through inspection experiences accumulated, and so on).

The operator selects one or a plurality of the flaw detection images required, according to the type of the defect determined, and displays the selected image or images in an aligned arrangement on a display screen 1 of an image display device as shown in FIG. 19 (Step S4).

If the type of the defect is D1, for example, the flaw detection image I1 and the flaw detection image I3 are selected, and both of the flaw detection images I1 and I3 are displayed in an side-by-side arrangement.

In this case, the flaw detection images I1 and I3 are each displayed in such a manner as to be superposed on, for example, partitioned regions R1 to R28 separated into 28 (4×7) regions by parting lines indicated by short dashed lines in FIG. 19. That is, the flaw detection images I1 and I3 are each divided into images on the partitioned regions R1 to R28.

Which of the flaw detection images should be selected according to the type of the defect, and how the selected images should be arranged, are judged based on the knowledge possessed by the operator (knowledge of the structure, shape, plate thickness and material of the wing, knowledge of the type of the defect, knowledge of the characteristics of the ultrasonic flaw detection test, knowledge acquired through inspection experiences accumulated thus far, and so on).

The operator changes the display range of the flaw detection images I1, I3.

Concretely, the starting position of X and Y coordinates displayed, and the ending position of the X and Y coordinates are changed to specify the partitioned regions to be displayed. Also, the display magnification is optimally changed to display, on an enlarged scale, an image in a predetermined range, for example, on the partitioned region R1 of the flaw detection images I1 and I3 (Step S5), as shown in FIG. 19.

To what degree the display magnification should be adjusted to be increased, and the image on which of the partitioned regions should be displayed, according to the type of the defect, are judged based on the knowledge possessed by the operator (knowledge of the structure, shape, plate thickness and material of the wing, knowledge of the type of the defect, knowledge of the characteristics of the ultrasonic flaw detection test, knowledge acquired through inspection experiences accumulated thus far, and so on).

In the state of FIG. 20, the image on the partitioned region R1 has merely been enlarged. Hence, the contrast between an image showing the defective site (a black-colored portion) and the sound site is not clear.

Thus, the operator makes a contrast adjustment for the enlarged images of the flaw detection images I1, I3 on the partitioned region R1 (FIG. 20) to enhance the contrast between the image of the sound site and the image of the defective site (Step S6).

To what degree the contrast should be adjusted, according to the type of the defect, is judged based on the knowledge possessed by the operator (knowledge of the structure, shape, plate thickness and material of the wing, knowledge of the type of the defect, knowledge of the characteristics of the ultrasonic flaw detection test, knowledge acquired through inspection experiences accumulated thus far, and so on).

The operator visually confirms the images (FIG. 21) obtained by enlarging, and adjusting the contrast of, the flaw detection images I1, I3 on the partitioned region R, to evaluate whether the defective site is present or not (Step S7).

The operator changes the display range of the flaw detection images I1, I3 from the image enlarged from the image on the partitioned region R1, successively, to the images enlarged from the images on the partitioned regions R2 to R28. When selecting the enlarged image on each of the partitioned regions R2 to R28, the operator performs the optimal changing of the display magnification, the contrast adjustment, and the visual inspection of the defective site, which are shown in Steps S5, S6 and S7, respectively, in accordance with the situation of the selected partitioned region.

After all the images on the partitioned regions R1 to R28 are inspected for the presence or absence of the defect D1 (Step S8), the type of the defect to be evaluated is changed to the defect of a different type (for example, defect D2) (Step S3).

For the defect D2, an inspection of the defective site is conducted in the same manner as for the defect D1.

In this manner, the type of the defect is sequentially changed, and after the inspection of the defective site is conducted for all types of defects, evaluation is completed (Step S9). Then, analysis work on the flaw detection images is completed (Step S10).

Depending on the type of the defect, the analysis of the flaw detection image in a specific partitioned region may be skipped, and this analysis may be made in a next partitioned region.

The reason is as follows: Knowledge or experience may teach, from the beginning, that depending on a specific image selected and a specific defect selected, defect detection in a specific partitioned region is impossible. In this case, the analysis of the flaw detection image in the specific partitioned region is skipped in order to cut down on time and labor.

PRIOR ART DOCUMENTS

Patent Documents

Patent Document 1: JP-A-9-251364

SUMMARY OF THE INVENTION

Problems to be Solved by the Invention

With the above-described conventional technique for inspecting the main wing with the use of the flaw detection image signal, the type or arrangement of the image displayed, the display range (magnification) or the contrast changes with the type of the defect or the partitioned region. It takes time to change these factors.

Furthermore, an inspector of small experience may err in the type or arrangement of the image displayed, the display range (magnification) or the contrast, posing the risk of an omission of defect detection occurring.

The present invention has been accomplished in the light of the above-described conventional technology. It is an object of the invention to provide an analytical apparatus for an ultrasonic flaw detection image which can reduce labor and time for conducting an inspection for a defect and can also detect a defect accurately regardless of the degree of mastery.

Means for Solving the Problems

An aspect of the present invention for solving the above problems is an analytical apparatus for an ultrasonic flaw detection image, comprising:

a flaw detection image signal database division storing a plurality of flaw detection image signals obtained by signal transformation of an identical flaw detection waveform signal by a plurality of different signal transformation techniques;

a flaw detection condition database division storing a flaw detection condition database constructed from many inspection procedure commands arranged in order of execution, the inspection procedure commands having, as information, a type of a defect to be inspected for, a flaw detection image used in accordance with the type of the defect to be inspected for, an arrangement pattern of the flaw detection image used, a display range showing a range of an image region displayed among image regions of the flaw detection image used, and contrast indicated values defining a contrast of an image in the display range; and a flaw detection image analyzer, wherein the flaw detection image analyzer captures the inspection procedure commands of the flaw detection condition database sequentially based on input commands from an outside, whenever the inspection procedure command is captured, captures from the flaw detection image signal database division the flaw detection image signal corresponding to the flaw detection image indicated by the captured inspection procedure command, and allows a display device to display the flaw detection image based on the flaw detection image signal in the arrangement pattern of the image indicated by the inspection procedure command, in the display range indicated by the inspection procedure command, and with the contrast indicated by the inspection procedure command.

Another aspect of the present invention is an analytical apparatus for an ultrasonic flaw detection image, comprising:

a flaw detection image signal database division storing a plurality of flaw detection image signals obtained by signal transformation of an identical flaw detection waveform signal by a plurality of different signal transformation techniques;

a flaw detection condition database division storing a first flaw detection condition database constructed from many inspection procedure commands arranged in order of execution, the inspection procedure commands having, as information, a type of a defect to be inspected for, and a display range showing a range of an image region displayed among image regions of a flaw detection image used; and a second flaw detection condition database defining the flaw detection image used, an arrangement pattern of the flaw detection image used, and contrast indicated values defining a contrast of an image in the display range, for each pattern comprising a combination of the type of the defect, a plate thickness, a shape, and a material;

a CAD model division having design data at least including data on a plate thickness, a shape and a material of an object to be inspected; and a flaw detection image analyzer, wherein the flaw detection image analyzer captures the inspection procedure commands of the first flaw detection condition database sequentially based on input commands from an outside, whenever the inspection procedure command is captured, captures from the CAD model division the plate thickness, shape, and material of a corresponding portion of the object to be inspected, which corresponds to the display range indicated by the captured inspection procedure command; incorporates the captured plate thickness, shape and material into the inspection procedure command; and captures by reference to the second flaw detection condition database the flaw detection image used, the arrangement pattern of the flaw detection image used, and the contrast indicated values defining the contrast of the image in the display range, which are defined for the pattern comprising the combination of the type of the defect, and the plate thickness, the shape, and the material captured from the CAD model division, and captures from the flaw detection image signal database division the flaw detection image signal corresponding to the flaw detection image used, and allows a display device to display the flaw detection image based on the flaw detection image signal in the captured arrangement pattern of the image, in the captured display range, and with the captured contrast.

Still another aspect of the present invention is an analytical apparatus for an ultrasonic flaw detection image, comprising:

a flaw detection image signal database division storing a plurality of flaw detection image signals obtained by signal transformation of an identical flaw detection waveform signal by a plurality of different signal transformation techniques;

a flaw detection condition database division storing a first flaw detection condition database constructed from many inspection procedure commands arranged in order of execution, the inspection procedure commands having, as information, a type of a defect to be inspected for, and a display range showing a range of an image region displayed among image regions of a flaw detection image used; and a second flaw detection condition database defining the flaw detection image used, an arrangement pattern of the flaw detection image used, and contrast indicated values defining a contrast of an image in the display range, for each pattern comprising a combination of the type of the defect, a plate thickness, a shape, and a material;

a CAD model division having design data at least including data on a shape and a material of an object to be inspected;

a plate thickness measuring device for measuring a plate thickness of the object to be inspected; and a flaw detection image analyzer, wherein the flaw detection image analyzer captures the inspection procedure commands of the first flaw detection condition database sequentially based on input commands from an outside, whenever the inspection procedure command is captured, captures from the CAD model division the shape and material of a corresponding portion of the object to be inspected, which corresponds to the display range indicated by the captured inspection procedure command; incorporates the captured shape and material into the inspection procedure command; simultaneously captures the plate thickness measured by the plate thickness measuring device as a plate thickness of the corresponding portion of the object to be inspected, which corresponds to the display range indicated by the captured inspection procedure command; and captures by reference to the second flaw detection condition database the flaw detection image used, the arrangement pattern of the flaw detection image used, and the contrast indicated values defining the contrast of the image in the display range, which are defined for the pattern comprising the combination of the type of the defect, and the plate thickness, the shape, and the material captured from the CAD model division and the plate thickness measuring device, and captures from the flaw detection image signal database division the flaw detection image signal corresponding to the flaw detection image used, and allows a display device to display the flaw detection image based on the flaw detection image signal in the captured arrangement pattern of the image, in the captured display range, and with the captured contrast.

Effects of the Invention

According to the present invention, in observing an ultrasonic flaw detection image to detect a defect, optimum images are displayed sequentially in an optimum arrangement pattern, in an optimum display range, and with an optimum contrast, in accordance with the defect to be inspected for. This saves an operator from having to manually select the image or change the arrangement pattern, the display range or the contrast, and can result in savings in labor and time for inspection.

Moreover, the defect can be detected accurately regardless of the degree of mastery of the operator, and an omission of defect detection is eliminated.

BRIEF DESCRIPTION OF THE DRAWINGS

FIG. 1 is a block diagram showing an analytical apparatus for an ultrasonic flaw detection image according to Embodiment 1 of the present invention.

FIG. 2 is a data drawing showing a flaw detection condition database used in Embodiment 1.

FIG. 5 is a data drawing showing a first flaw detection condition database used in Embodiment 2.

FIG. 6 is a data drawing showing a second flaw detection condition database used in Embodiment 2.

MODE FOR CARRYING OUT THE INVENTION

Figure 3:
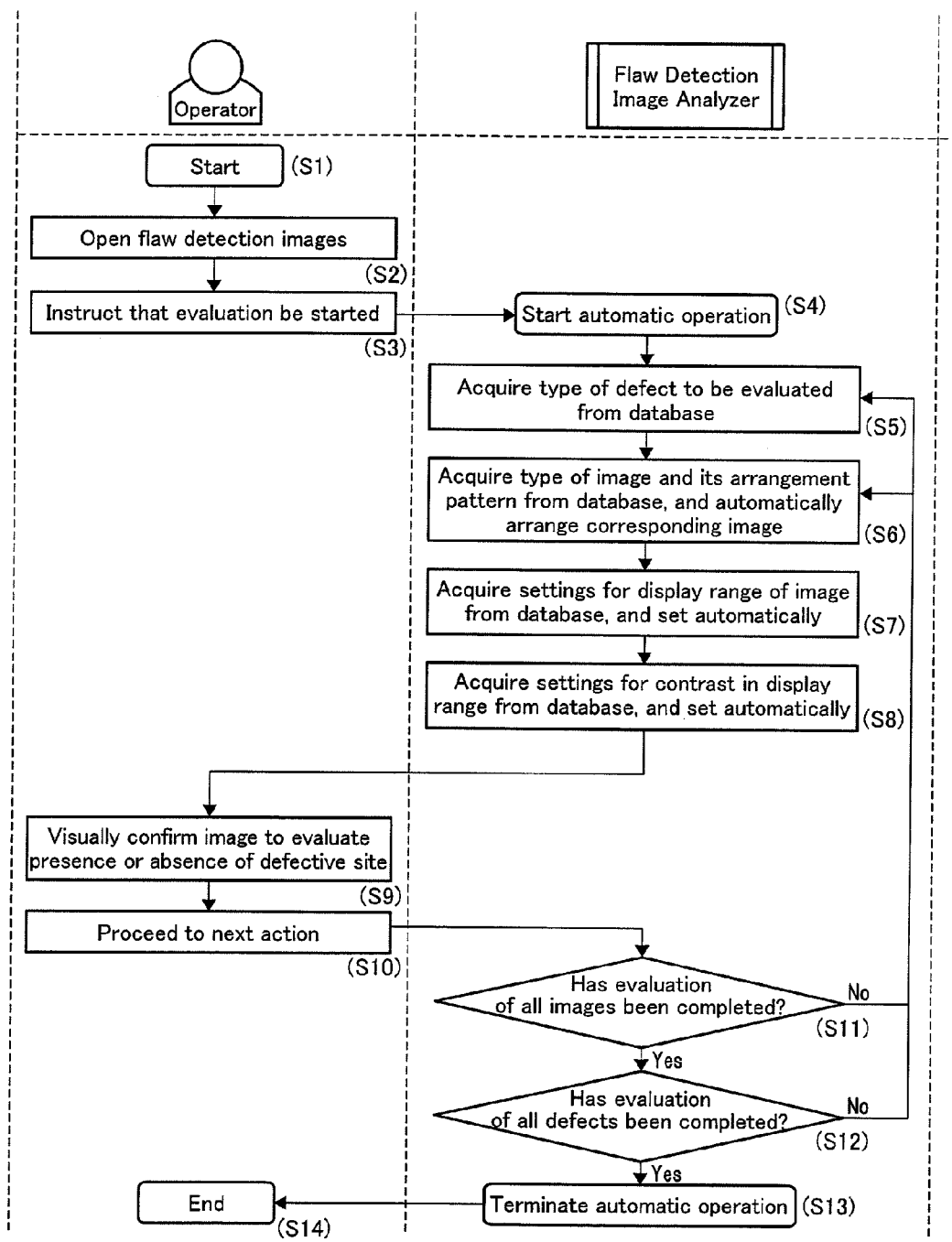
FIG. 3 is a flowchart showing the operating state of Embodiment 1.

Modes for carrying out the present invention will be described in detail based on embodiments.

Embodiment 1

FIG. 1 is a block diagram showing an analytical apparatus for an ultrasonic flaw detection image according to Embodiment 1 of the present invention. This analytical apparatus for an ultrasonic flaw detection image is composed of a flaw detection image analyzer 10, an input device 20, an image display device 30, a flaw detection condition database division 40, and a flaw detection image signal database division 50.

The flaw detection image signal database division 50 has a plurality of flaw detection image signals i1 to in stored beforehand. These plural flaw detection image signals i1 to in are obtained by signal transformation of a flaw detection waveform signal, which has been acquired during the movement of an ultrasonic probe along a flaw detection path set on the main wing of an aircraft, by a plurality of different signal transformation techniques (a TOF image signal transformation technique, an AMP image signal transformation technique, and signal transformation techniques rendered different in gate from these signal transformation techniques).

These plural flaw detection image signals i1 to in are fed to the image display device 30 via the flaw detection image analyzer 10, whereby flaw detection images I1 to In can be displayed on a display screen 31.

The flaw detection condition database division 40 has, prestored therein, a flaw detection condition database as shown in FIG. 2. This flaw detection condition database is a database constructed from many inspection procedure commands C arranged in order of execution.

Each of the inspection procedure commands C is composed of the type of a defect to be inspected for, a flaw detection image used according to the type of the defect to be inspected for, the arrangement pattern of the flaw detection image used, a display range showing the range of an image region displayed among the image regions of the flaw detection image used, and contrast indicated values (maximum value and minimum value of contrast) defining the contrast of the image within the display range.

The inspection procedure command C1, for example, is composed of information showing that the type of the defect to be inspected for is D1; the flaw detection image used according to the type D1 of the defect to be inspected for is I1; the arrangement pattern of the flaw detection image I1 used is maximum enlargement of one image on the screen; the display range showing the range of the image region displayed among the image regions of the flaw detection image I1 used is a range in which the starting position X1 on the X axis is 0, the ending position X2 on the X axis is 10, the starting position Y1 on the Y axis is 0, and the ending position Y2 on the Y axis is 20; and the contrast minimum value of the contrast indicated values defining the contrast of the image in the display range is 20, while the contrast maximum value of the contrast indicated values is 40.

The inspection procedure command C101, for example, is composed of information showing that the type of the defect to be inspected for is D2; the flaw detection images used according to the type D2 of the defect to be inspected for are I1 and I4; the arrangement pattern of the flaw detection images I1 and I4 used is display of the two images in a laterally aligned arrangement; the display range showing the range of the image region displayed among the image regions of the flaw detection images I1, I4 used is a range in which the starting position X1 on the X axis is 0, the ending position X2 on the X axis is 10, the starting position Y1 on the Y axis is 0, and the ending position Y2 on the Y axis is 20; and the contrast minimum value of the contrast indicated values defining the contrast of the image in the display range is 20 for the flaw detection image I1 and 30 for the flaw detection image I4, while the contrast maximum value of the contrast indicated values is 40 for the flaw detection image I2 and 50 for the flaw detection image I4.

In the flaw detection condition database, the inspection procedure commands (e.g., commands C1, C2, C3, C4 ...) for inspecting for the defect of the same type (for example, defect D1) are set consecutively in order of execution.

Further, the display ranges of the plurality of inspection procedure commands set consecutively in order of execution for detecting the defect of the same type are set such that the display range instructed by the succeeding inspection procedure command is positionally displaced from the display range instructed by the preceding inspection procedure command.

Each of the inspection procedure commands C has, predetermined therein, the flaw detection image used, the arrangement pattern of the image, the display range (magnification), and the contrast, according to the type of the defect, so that the defect can be detected optimally in consideration of the type of the defect and the shape, plate thickness and material of each site.

If necessary, the contents of each inspection procedure command C can be modified. This modification can be made by the entry of modification data by the operator via the input device 20.

The operator enters an instruction on start of the inspection into the flaw detection image analyzer 10 via the input device 20, thereby being capable of conducting the flaw detection test.

Next, the operating state of Embodiment 1 will be described with reference to a flowchart shown in FIG. 3.

In starting inspection work (Step S1 in FIG. 3), the operator enters commands to open the flaw detection images and start evaluation into the flaw detection image analyzer 10 via the input device 20 (Steps S2, S3).

The flaw detection image analyzer 10 takes in or captures the flaw detection image signals i1 to in from the flaw detection image signal database division 50, and stores the flaw detection image signals i1 to in into the memory within the flaw detection image analyzer 10.

An automatic operation is started by the flaw detection image analyzer 10 (Step S4).

The flaw detection image analyzer 10 refers to the flaw detection condition database of the flaw detection condition database division 40, and carries out the inspections sequentially based on the information indicated by the inspection procedure commands C.

The flaw detection image analyzer 10 first captures the inspection procedure command C1, thereby knowing that the type of the defect to be inspected for is D1 (Step S5). The flaw detection image analyzer 10 also knows that the flaw detection image used is I1, and that the one flaw detection image I1 will be displayed in a maximally enlarged size on the screen, and displays the flaw detection image I1 based on the flaw detection image signal i1 in the maximum size on the display screen 31 of the image display device 30 (Step S6).

The flaw detection image analyzer 10 also acquires, based on the inspection procedure command C1, the display range (i.e., the range in which the starting position X1 on the X axis is 0, the ending position X2 on the X axis is 10, the starting position Y1 on the Y axis is 0, and the ending position Y2 on the Y axis is 20), and displays the image in the region of the above display range in the flaw detection image I1, in the maximum size, on the display screen 31 (Step S7).

Furthermore, the flaw detection image analyzer 10 acquires, based on the inspection procedure command C1, the contrast indicated values (contrast minimum value is 20, and contrast maximum value is 40), and adjusts the contrast of the image in the region of the above display range in the flaw detection image I1, which has been displayed in the maximum size on the display screen 31, according to the above contrast indicated values (Step S8).

The operator visually confirms the flaw detection image displayed on the display screen 31 of the image display device 30 (image displayed in the maximum size on the display screen 31 with a specific contrast in a display range in a specific region (at a specific magnification) designated by the inspection procedure command C1 in the flaw detection image I1) to evaluate whether the defect D1 is present or absent (Step S9).

After evaluating the presence or absence of the defect D1 by visual inspection, the operator issues a command for proceeding to a next action (Step S10).

The flaw detection image analyzer 10 captures the inspection procedure command C2, performs the actions of Steps S5 to S8 based on the inspection procedure command C2, and displays the image of a specific contrast, in the display range in the specific region of the flaw detection image I1 designated by the inspection procedure command C2, on a maximally enlarged scale, on the display screen 31.

The operator visually confirms the flaw detection image displayed on the display screen 31 of the image display device 30 (image displayed in the maximum size on the display screen 31 with a specific contrast in a display range in a specific region (at a specific magnification) designated by the inspection procedure command C2 in the flaw detection image I1) to evaluate whether the defect D1 is present or absent (Step S9).

After evaluating the presence or absence of the defect D1 by visual inspection, the operator issues a command to proceed to a next action (Step S10).

Such actions are also performed under the inspection procedure commands C3, C4, . . . which have been set consecutively.

After the evaluation of the entire screen is completed in connection with the inspection for the presence or absence of the defect D1 (Step S11), the flaw detection image analyzer 10 captures the inspection procedure command C101, which is the inspection procedure command to inspect for the defect D2, in order to inspect for the presence or absence of the next defect D2.

The flaw detection image analyzer 10 first captures the inspection procedure command C101, thereby knowing that the type of the defect to be inspected for is D2 (Step S5). The flaw detection image analyzer 10 also knows that the flaw detection images used are I1, I4, and that the two flaw detection images I1 and I4 will be displayed in a laterally aligned arrangement on the screen, and displays the flaw detection images I1, I4 based on the flaw detection image signals i1, i4 in the laterally aligned arrangement on the display screen 31 of the image display device 30 (Step S6).

The flaw detection image analyzer 10 also acquires, based on the inspection procedure command C101, the display range (i.e., the range in which the starting position X1 on the X axis is 0, the ending position X2 on the X axis is 10, the starting position Y1 on the Y axis is 0, and the ending position Y2 on the Y axis is 20), and displays the images in the region of the above display range in the flaw detection images I1, I4, in the laterally aligned arrangement, on the display screen 31 (Step S7).

Furthermore, the flaw detection image analyzer 10 acquires, based on the inspection procedure command C101, the contrast indicated values (contrast minimum value is 20 for the flaw detection image I1 and 30 for the flaw detection image I4, and contrast maximum value is 40 for the flaw detection image I1 and 50 for the flaw detection image I4), and adjusts the contrast of the images in the region of the above display range in the flaw detection images I1, I4, which have been displayed in the laterally aligned arrangement on the display screen 31, according to the above contrast indicated values (Step S8).

The operator visually confirms the flaw detection images displayed on the display screen 31 of the image display device 30 (images displayed in the laterally aligned arrangement on the display screen 31 with the specific contrast in the display range in the specific region (at a specific magnification) designated by the inspection procedure command C101 in the flaw detection images I1, I4) to evaluate whether the defect D2 is present or absent (Step S9).

After evaluating the presence or absence of the defect D2 by visual inspection, the operator issues a command to proceed to a next action (Step S10).

Under this command, the flaw detection image analyzer 10 captures the inspection procedure command C102, performs the actions of Steps S5 to S8 based on the inspection procedure command C102, and displays the images of the specific contrast, in the display range in the specific region of the flaw detection images I1, I4 designated by the inspection procedure command C102, in the laterally aligned arrangement, on the display screen 31.

The operator visually confirms the flaw detection images displayed on the display screen 31 of the image display device 30 (images displayed in the laterally aligned arrangement on the display screen 31 with the specific contrast in the display range in the specific region (at the specific magnification) designated by the inspection procedure command C102 in the flaw detection images I1, I4) to evaluate whether the defect D2 is present or absent (Step S9).

After evaluating the presence or absence of the defect D2 by visual inspection, the operator issues a command to proceed to a next action (Step S10).

Such actions are also performed under the inspection procedure commands C103, . . . which have been set consecutively.

After the evaluation of the entire screen is completed in connection with the inspection for the presence or absence of the defect D2 (Step S11), the flaw detection image analyzer 10 captures the inspection procedure command CN, which is the inspection procedure command to inspect for the defect D3, in order to inspect for the presence or absence of the next defect D3, and displays images upon the same processings as mentioned above. The operator visually confirms the displayed images, and can thereby evaluate whether the defect is present or absent.

When the inspection procedure command C has been executed up to the end to complete the evaluation of all the defects (Step S12), the flaw detection image analyzer 10 terminates the automatic operation (Step S13), whereupon the analysis work on the flaw detection images (defect detection work) is completed (Step S14).

It is possible to make setting such that when the operator has visually confirmed the defect, the site and type of the defect are stored into the flaw detection image analyzer 10 and, after completion of work on the defect inspection, the stored defective sites are displayed on the display screen 31 by the type of the defect.

In the above-described manner, the flaw detection image analyzer 10 performs the automatic operation, whereby the images of the optimal type are displayed sequentially on the display screen 31 of the image display device 30 in the optimal arrangement state, in the optimal display range (magnification) with the optimal contrast, in accordance with the type of each defect. Thus, the operator can conduct the inspection for the defect while looking at the display screen, without the need to select the image or to carry out an operation for changing the display position, display magnification, or the like.

Hence, the inspection for the defect can be easily performed in a short time, and even an inspector with little experience can conduct the defect inspection accurately without an omission of inspection.

Embodiment 2

Figure 4:
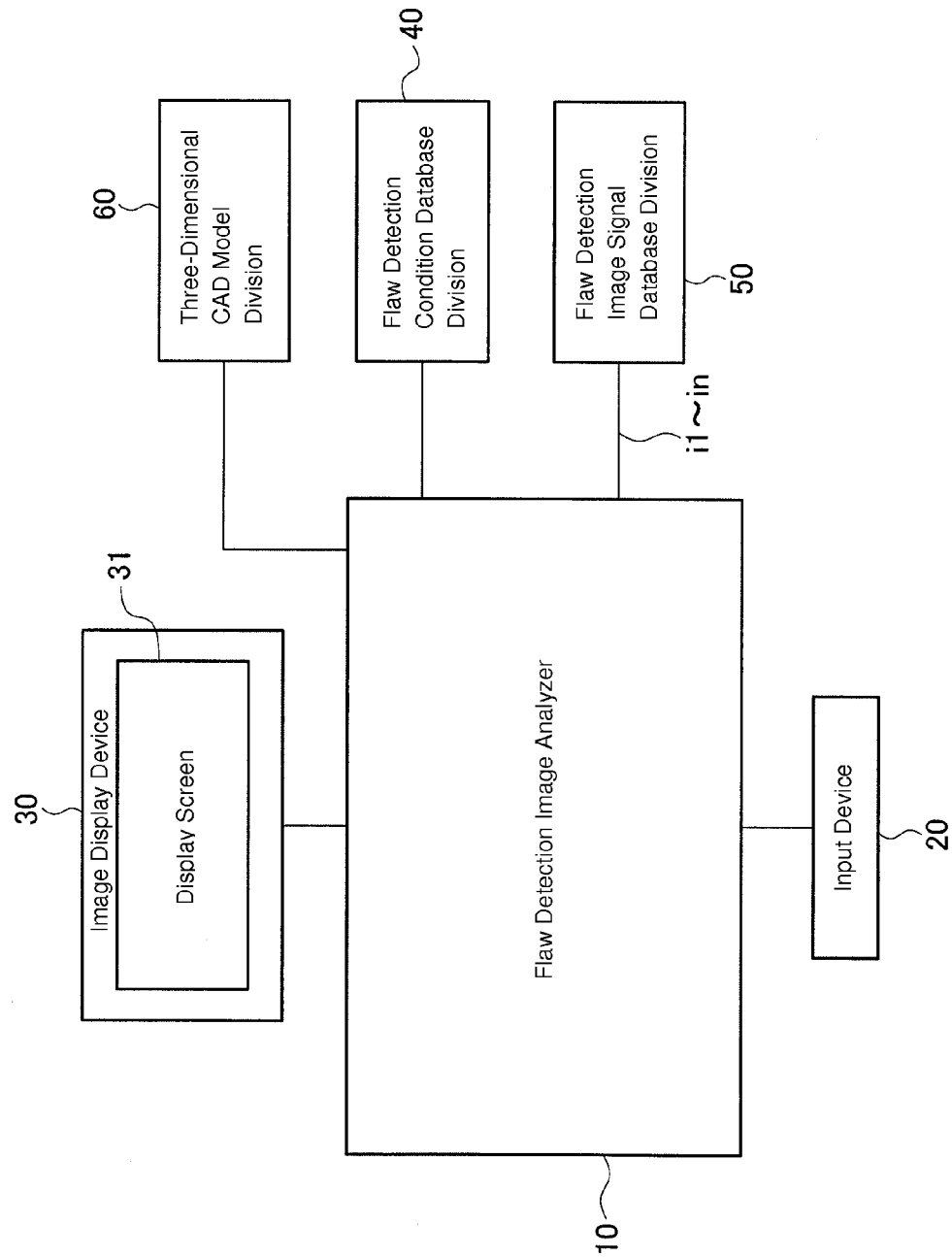
FIG. 4 is a block diagram showing an analytical apparatus for an ultrasonic flaw detection image according to Embodiment 2 of the present invention.

FIG. 4 is a block diagram showing an analytical apparatus for an ultrasonic flaw detection image according to Embodiment 2 of the present invention. This analytical apparatus for an ultrasonic flaw detection image is composed of a flaw detection image analyzer 10, an input device 20, an image display device 30, a flaw detection condition database division 40, a flaw detection image signal database division 50, and a three-dimensional CAD model division 60.

The three-dimensional CAD model division 60 has in storage various data necessary for designing an object to be inspected (e.g., the main wing of an aircraft), for example, design data, such as plate thickness, shape, material, dimensions, and structure.

The flaw detection image signal database division 50 has a plurality of flaw detection image signals i1 to in stored beforehand. These plural flaw detection image signals i1 to in are obtained by signal transformation of a flaw detection waveform signal, which has been acquired during the movement of an ultrasonic probe along a flaw detection path set on the main wing of an aircraft, by a plurality of different signal transformation techniques (a TOF image signal transformation technique, an AMP image signal transformation technique, and signal transformation techniques rendered different in gate from these signal transformation techniques).

These flaw detection image signals i1 to in are fed to the image display device 30 via the flaw detection image analyzer 10, whereby flaw detection images I1 to In can be displayed on a display screen 31.

The flaw detection condition database division 40 has, prestored therein, a first flaw detection condition database DB1 as shown in FIG. 5, and a second flaw detection condition database DB2 as shown in FIG. 6.

The first flaw detection condition database DB1 shown in FIG. 5 is a database constructed from many inspection procedure commands C arranged in order of execution. In FIG. 5, data such as plate thickness, shape and material are already described, but initially, these data, i.e., plate thickness, shape and material, have not been described. As will be described later, these data are taken in or captured by reference to CAD data stored in the three-dimensional CAD model division 60.

The first flaw detection condition database DB1 shown in FIG. 5 will be described. Each of the inspection procedure commands C is composed of the type of a defect to be inspected for, and a display range showing the range of an image region displayed among the image regions of the flaw detection image.

As will be described later, in executing each inspection procedure command C, the flaw detection image analyzer 10 acquires the plate thickness, shape and material of the corresponding portion of the object to be inspected (main wing), which corresponds to the display range, from the CAD data, and integrates (records) them into each inspection procedure command C.

The inspection procedure command C1, for example, is composed of information showing that the type of the defect to be inspected for is D1; and the display range showing the range of the image region displayed among the image regions of the flaw detection image used is a range in which the starting position X1 on the X axis is 0, the ending position X2 on the X axis is 10, the starting position Y1 on the Y axis is 0, and the ending position Y2 on the Y axis is 20.

The inspection procedure command C101, for example, is composed of information showing that the type of the defect to be inspected for is D2; and the display range showing the range of the image region displayed among the image regions of the flaw detection image used is a range in which the starting position X1 on the X axis is 0, the ending position X2 on the X axis is 10, the starting position Y1 on the Y axis is 0, and the ending position Y2 on the Y axis is 20.

In the first flaw detection condition database DB1, the inspection procedure commands (e.g., commands C1, C2, C3, C4 . . . ) for inspecting for the defect of the same type (for example, defect D1) are set consecutively in order of execution.

Further, the display ranges of the plurality of inspection procedure commands set consecutively in order of execution for detecting the defect of the same type are set such that the display range indicated by the succeeding inspection procedure command is positionally displaced from the display range indicated by the preceding inspection procedure command.

Next, the second flaw detection condition database DB2 shown in FIG. 6 will be described. The second flaw detection condition database DB2 defines a flaw detection image used, the arrangement pattern of the flaw detection image used, and contrast indicated values (minimum value and maximum value of contrast) defining the contrast of the image in the display range, for each pattern comprising a combination of the type of the defect, plate thickness, shape, and material.

The second flaw detection condition database DB2 has, predetermined therein, the flaw detection image used, the arrangement pattern of the image, and the contrast, according to the type of the defect, so that the defect can be detected optimally in consideration of the type of the defect, the shape, plate thickness, and material of each site.

If necessary, the contents of the flaw detection condition databases DB1, DB2 can be modified. This modification can be made by the entry of modification data by the operator via the input device 20.

Figure 7:
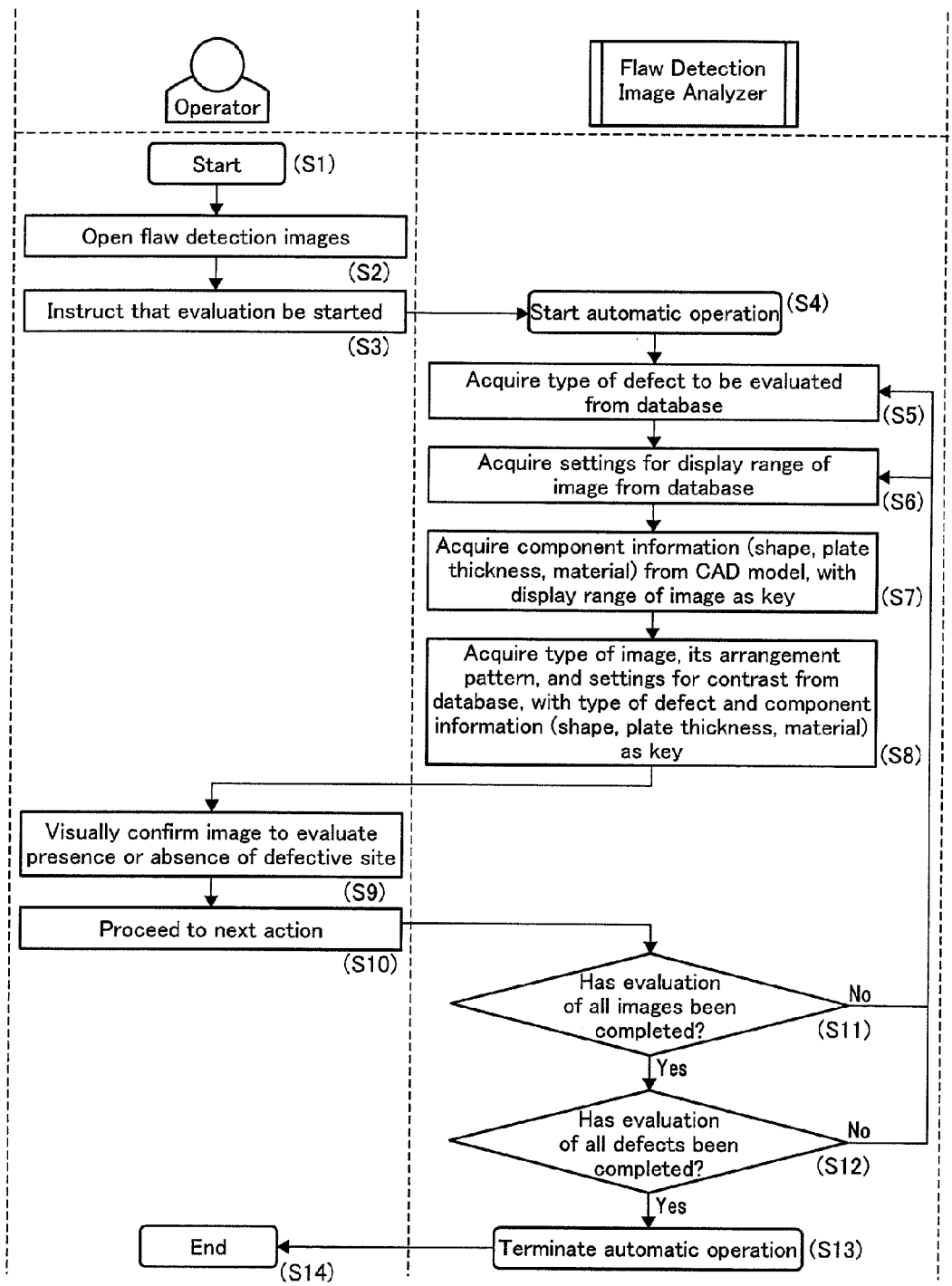
FIG. 7 is a flowchart showing the operating state of Embodiment 2.

Next, the operating state of Embodiment 2 will be described with reference to a flowchart shown in FIG. 7.

In starting inspection work (Step S1 in FIG. 7), the operator enters commands to open the flaw detection images and issue instructions to start evaluation, into the flaw detection image analyzer 10 via the input device 20 (Steps S2, S3).

The flaw detection image analyzer 10 captures the flaw detection image signals i1 to in from the flaw detection image signal database division 50, and stores the flaw detection image signals i1 to in into the memory within the flaw detection image analyzer 10.

An automatic operation is started by the flaw detection image analyzer 10 (Step S4).

The flaw detection image analyzer 10 refers to the first flaw detection condition database DB1 of the flaw detection condition database division 40, and carries out the inspection sequentially based on the information indicated by the inspection procedure commands C.

The flaw detection image analyzer 10 first captures the inspection procedure command C1, thereby knowing that the type of the defect to be inspected for is D1 (Step S5). The flaw detection image analyzer 10 also acquires the display range (the range in which the starting position X1 on the X axis is 0, the ending position X2 on the X axis is 10, the starting position Y1 on the Y axis is 0, and the ending position Y2 on the Y axis is 20) (Step S6).

Then, the flaw detection image analyzer 10 captures the plate thickness, shape, and material of the corresponding portion of the object to be inspected (main wing), which corresponds to the display range acquired in Step S6, by reference to the CAD data stored in the three-dimensional CAD model division 60, and stores the captured CAD data (the plate thickness is 10, the shape is F1, and the material is M1) in a form built into the inspection procedure command C1 (Step S7).

The flaw detection image analyzer 10 refers to the second flaw detection condition database DB2 of the flaw detection condition database division 40, acquiring the information set in the pattern comprising a combination of the defect type D1, plate thickness (10), shape (F1) and material (M1), namely, the information that the flaw detection image used is I1, the arrangement pattern of the flaw detection image I1 used is the maximum enlargement of a single image on the screen, the contrast minimum value of the contrast indicated values defining the contrast of the image in the display range is 20, and the contrast maximum value is 40 (Step S8).

By referring to the inspection procedure command C1 of the first flaw detection condition database DB1, the CAD data stored in the three-dimensional CAD model division 60, and the second flaw detection condition database DB2 in the above-mentioned manner, it is possible to acquire the information that the type of the defect to be inspected for is D1, the flaw detection image used in accordance with the type D1 of the defect to be inspected for is I1, the arrangement pattern of the flaw detection image I1 used is the maximum enlargement of a single image on the screen, the display range showing the range of the image region to be displayed among the image regions of the flaw detection image I1 used is the range in which the starting position X1 on the X axis is 0, the ending position X2 on the X axis is 10, the starting position Y1 on the Y axis is 0, and the ending position Y2 on the Y axis is 20, and the contrast minimum value of the contrast indicated values defining the contrast of the image in the display range is 20, and the contrast maximum value is 40.

Based on the so acquired information, the flaw detection image analyzer 10 maximally enlarges a single image, of the flaw detection image I1 based on the flaw detection image signal i1, in the above display range (the starting position X1 on the X axis is 0, the ending position X2 on the X axis is 10, the starting position Y1 on the Y axis is 0, and the ending position Y2 on the Y axis is 20) with the above contrast (the contrast minimum value is 20, and the contrast maximum value is 40), and displays the enlarged image on the display screen 31 of the image display device 30.

The operator visually confirms the flaw detection image displayed on the display screen 31 of the image display device 30 (the image displayed in a maximum size on the display screen 31 with a specific contrast in the display range in a specific region (magnification) of the flaw detection image I1) to evaluate whether the defect D1 is present or not (Step S9).

After evaluating the presence or absence of the defect D1 visually, the operator issues a command to proceed to a next action (Step S10).

The flaw detection image analyzer 10 captures the inspection procedure command C2, and performs the actions of Steps S5 to S8 by referring to the inspection procedure command C2, the CAD data stored in the three-dimensional CAD model division 60, and the second flaw detection condition database DB2. By so doing, the flaw detection image analyzer 10 maximally enlarges a single image, of the flaw detection image I1, in a display range in a specific region (the starting position X1 on the X axis is 10, the ending position X2 on the X axis is 20, the starting position Y1 on the Y axis is 0, and the ending position Y2 on the Y axis is 20) with a specific contrast (the contrast minimum value is 20, and the contrast maximum value is 40), and displays the enlarged image on the display screen 31.

The operator visually confirms the flaw detection image displayed on the display screen 31 of the image display device 30 (the image displayed in the maximum size on the display screen 31 with the specific contrast in the display range in the specific region (magnification) of the flaw detection image I1) to evaluate whether the defect D1 is present or not (Step S9).

After visually evaluating the presence or absence of the defect D1, the operator issues a command to proceed to a next action (Step S10).

Such actions are also performed under the inspection procedure commands C3, C4 . . . , which have been set consecutively, by reference to the CAD stored in the three-dimensional CAD model division 60, and the second flaw detection condition database DB2.

After the evaluation of the entire screen is completed in connection with the inspection for the presence or absence of the defect D1 (Step S11), the flaw detection image analyzer 10 captures the inspection procedure command C101, which is the inspection procedure command to inspect for the defect D2, in order to inspect for the presence or absence of the next defect D2.

The flaw detection image analyzer 10 first captures the inspection procedure command C101, thereby knowing that the type of the defect to be inspected for is D2 (Step S5). The flaw detection image analyzer 10 also captures the display range (the range in which the starting position X1 on the X axis is 0, the ending position X2 on the X axis is 10, the starting position Y1 on the Y axis is 0, and the ending position Y2 on the Y axis is 20) (Step S6).

Then, the flaw detection image analyzer 10 captures the plate thickness, shape, and material of the corresponding portion of the object to be inspected (main wing), which corresponds to the display range acquired in Step S6, by reference to the CAD data stored in the three-dimensional CAD model division 60, and stores the captured CAD data (the plate thickness is 10, the shape is F2, and the material is M2) in a form built into the inspection procedure command C101 (Step S7).

The flaw detection image analyzer 10 refers to the second flaw detection condition database DB2 of the flaw detection condition database division 40, acquiring the information set in the pattern comprising a combination of the defect type D2, plate thickness (10), shape (F2) and material (M2), namely, the information that the flaw detection images used are I1 and I3, the arrangement pattern of the flaw detection images I1, I2 used is the placement of the two images in a laterally aligned arrangement, the contrast minimum value of the contrast indicated values defining the contrast of the image in the display range is 20 for the flaw detection image I1 and 30 for the flaw detection image I3, and the contrast maximum value is 40 for the flaw detection image I1 and 50 for the flaw detection image I3 (Step S8).

By referring, in the above-mentioned manner, to the inspection procedure command C2 of the first flaw detection condition database DB1, the CAD data stored in the three-dimensional CAD model division 60, and the second flaw detection condition database DB2, it becomes possible to acquire the information showing that the type of the defect to be inspected for is D2, the flaw detection images used in accordance with the type D2 of the defect to be inspected for are I1, I3, the arrangement pattern of the flaw detection images I1, I3 used is the placement of the two images in the laterally aligned arrangement, the display range showing the range of the image region displayed among the image regions of the flaw detection images I1, I3 used is the range in which the starting position X1 on the X axis is 0, the ending position X2 on the X axis is 10, the starting position Y1 on the Y axis is 0, and the ending position Y2 on the Y axis is 20, and the contrast minimum value of the contrast indicated values defining the contrast of the image in the display range is 20 for the flaw detection image I1 and 30 for the flaw detection image I3, and the contrast maximum value is 40 for the flaw detection image I1 and 50 for the flaw detection image I3.

Based on the so acquired information, the flaw detection image analyzer 10 displays two images in a laterally aligned arrangement on the display screen 31 of the image display device 30, the two images being images of the flaw detection images I1, I3 based on the flaw detection image signals i1, i3 and being in the above display range (the starting position X1 on the X axis is 0, the ending position X2 on the X axis is 10, the starting position Y1 on the Y axis is 0, and the ending position Y2 on the Y axis is 20) with the above contrast (the contrast minimum value is 20 for the flaw detection image I1 and 30 for the flaw detection image I3, and the contrast maximum value is 40 for the flaw detection image I1 and 50 for the flaw detection image I3).

The operator visually confirms the flaw detection images displayed on the display screen 31 of the image display device 30 (the images displayed in a laterally aligned arrangement on the display screen 31 with the specific contrast in the display range in the specific region (magnification) of the flaw detection images I1, I3) to evaluate whether the defect D2 is present or not (Step S9).

After visually evaluating the presence or absence of the defect D2, the operator issues a command to proceed to a next action (Step S10).

Under this command, the flaw detection image analyzer 10 captures the inspection procedure command C102, and performs the actions of Steps S5 to S8 while referring to the inspection procedure command C102, the CAD data stored in the three-dimensional CAD model division 60, and the second flaw detection condition database DB2. By so doing, the flaw detection image analyzer 10 displays two images in a laterally aligned arrangement on the display screen 31, the two images being images of the flaw detection images I1, I3 and being in a display range in a specific region (the starting position X1 on the X axis is 10, the ending position X2 on the X axis is 20, the starting position Y1 on the Y axis is 0, and the ending position Y2 on the Y axis is 20) with a specific contrast (the contrast minimum value is 20 for the flaw detection image I1 and 30 for the flaw detection image I3, and the contrast maximum value is 40 for the flaw detection image I1 and 50 for the flaw detection image I3).

The operator visually confirms the flaw detection images displayed on the display screen 31 of the image display device 30 (the images displayed in a laterally aligned arrangement on the display screen 31 with the specific contrast in the display range in the specific region (magnification) of the flaw detection images I1, I3) to evaluate whether the defect D2 is present or not (Step S9).

After visually evaluating the presence or absence of the defect D2, the operator issues a command to proceed to a next action (Step S10).

Such actions are also performed under the inspection procedure commands C103 . . . , which have been set consecutively, by reference to the CAD data stored in the three-dimensional CAD model division 60, and the second flaw detection condition database DB2.

After the evaluation of the entire screen is completed in connection with the inspection for the presence or absence of the defect D2 (Step S11), the flaw detection image analyzer 10 captures the inspection procedure command CN, which is the inspection procedure command to inspect for the defect D3, in order to inspect for the presence or absence of the next defect D3. The flaw detection image analyzer 10 performs the same processings as mentioned above, and displays the images. The operator visually confirms the displayed images, and can thereby evaluate whether the defect is present or not.

After the inspection procedure command C is executed up to the end and the evaluation of all the defects is completed (Step S12), the flaw detection image analyzer 10 terminates the automatic operation (Step S13), and then the analysis work on the flaw detection images (defect detection work) is completed (Step S14).

It is possible to make settings such that when the operator has visually confirmed the defect, the site and type of the defect are stored into the flaw detection image analyzer 10 and, after completion of work on the defect inspection, the stored defective sites are displayed on the display screen 31 by the type of the defect.

In the above-described manner, the flaw detection image analyzer 10 performs the automatic operation, whereby the images of the optimal type in the optimal arrangement state, in the optimal display range (magnification) with the optimal contrast are sequentially displayed on the display screen 31 of the image display device 30 in accordance with the type of each defect. Thus, the operator can conduct the inspection for the defect while looking at the display screen, without the need to select the image or to carry out an operation for changing the display position, display magnification, or the like.

Hence, the inspection for the defect can be easily performed in a short time, and even an inspector with little experience can conduct the defect inspection accurately without an omission of inspection.

Based on the type of the defect, plate thickness, shape, and material, moreover, the flaw detection image used, and the arrangement pattern and contrast of the image are acquired from the second flaw detection condition database DB2. This obviates the necessity of registering the flaw detection image used, and the arrangement pattern and contrast of the image, individually on all the inspection procedure commands. Thus, it becomes easy to create a flaw detection condition database as a whole.

Embodiment 3

Figure 8:
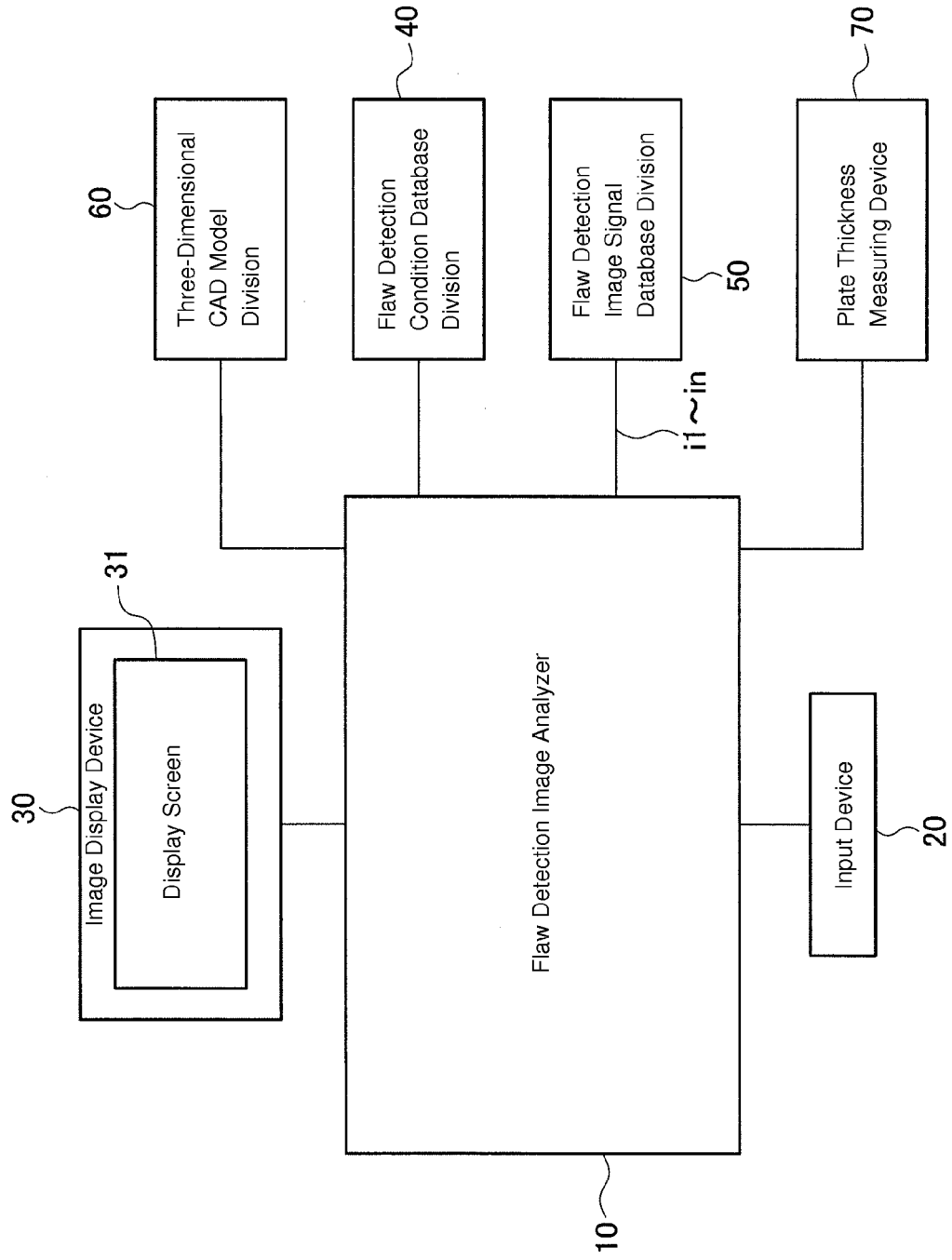
FIG. 8 is a block diagram showing an analytical apparatus for an ultrasonic flaw detection image according to Embodiment 3 of the present invention.

FIG. 8 is a block diagram showing an analytical apparatus for an ultrasonic flaw detection image according to Embodiment 3 of the present invention. This analytical apparatus for an ultrasonic flaw detection image is composed of a flaw detection image analyzer 10, an input device 20, an image display device 30, a flaw detection condition database division 40, a flaw detection image signal database division 50, a three-dimensional CAD model division 60, and a plate thickness measuring device 70.

The plate thickness measuring device 70 actually measures the plate thickness of an object to be inspected (for example, the main wing of an aircraft), and outputs its measured value (plate thickness).

The three-dimensional CAD model division 60 has in storage various data necessary for designing the object to be inspected (e.g., the main wing of an aircraft), for example, design data, such as plate thickness, shape, material, dimensions, and structure.

The flaw detection image signal database division 50 has a plurality of flaw detection image signals i1 to in stored beforehand. These plural flaw detection image signals i1 to in are obtained by signal transformation of a flaw detection waveform signal, which has been acquired during the movement of an ultrasonic probe along a flaw detection path set on the main wing of an aircraft, by a plurality of different signal transformation techniques (a TOF image signal transformation technique, an AMP image signal transformation technique, and signal transformation techniques rendered different in gate from these signal transformation techniques).

These flaw detection image signals i1 to in are fed to the image display device 30 via the flaw detection image analyzer 10, whereby flaw detection images I1 to In can be displayed on a display screen 31.

The flaw detection condition database division 40 has, prestored therein, a first flaw detection condition database DB1 as shown in FIG. 5, and a second flaw detection condition database DB2 as shown in FIG. 6, as in Embodiment 2.

The first flaw detection condition database DB1 shown in FIG. 5 is a database constructed from many inspection procedure commands C being arranged in order of execution. In FIG. 5, data such as plate thickness, shape and material are already described, but initially, these data, plate thickness, shape and material, have not been stored. As will be described later, the shape and material are captured by reference to CAD data stored in the three-dimensional CAD model division 60, while the plate thickness is captured as a measured value (plate thickness) obtained by actually measuring the plate thickness of the object to be inspected in the wing by means of the plate thickness measuring device 70.

The first flaw detection condition database DB1 shown in FIG. 5 will be described. Each inspection procedure command C is composed of the type of a defect to be inspected for, and a display range showing the range of an image region displayed among the image regions of the flaw detection image.

As will be described later, in executing each inspection procedure command C, the flaw detection image analyzer 10 acquires the shape and material of the corresponding portion of the object to be inspected (main wing), which corresponds to the display range, from the CAD data, and integrates (records) them into each inspection procedure command C. The flaw detection image analyzer 10 also acquires the plate thickness actually measured by the plate thickness measuring device 70, as the plate thickness of the corresponding portion of the object to be inspected (main wing), which corresponds to the display range, and integrates (records) it into each inspection procedure command C.

The inspection procedure command C1, for example, is composed of information showing that the type of the defect to be inspected for is D1; and the display range showing the range of the image region displayed among the image regions of the flaw detection image used is a range in which the starting position X1 on the X axis is 0, the ending position X2 on the X axis is 10, the starting position Y1 on the Y axis is 0, and the ending position Y2 on the Y axis is 20.

The inspection procedure command C101, for example, is composed of information showing that the type of the defect to be inspected for is D2; and the display range showing the range of the image region displayed among the image regions of the flaw detection image used is a range in which the starting position X1 on the X axis is 0, the ending position X2 on the X axis is 10, the starting position Y1 on the Y axis is 0, and the ending position Y2 on the Y axis is 20.

In the first flaw detection condition database DB1, the inspection procedure commands (e.g., commands C1, C2, C3, C4 . . . ) for inspecting for the defect of the same type (for example, defect D1) are set consecutively in order of execution.

Further, the display ranges of the plurality of inspection procedure commands set consecutively in order of execution for detecting the defect of the same type are set such that the display range indicated by the succeeding inspection procedure command is positionally displaced from the display range indicated by the preceding inspection procedure command.

Next, the second flaw detection condition database DB2 shown in FIG. 6 will be described. The second flaw detection condition database DB2 specifies a flaw detection image used, the arrangement pattern of the flaw detection image used, and contrast indicated values (maximum value and minimum value of contrast) defining the contrast of the image in the display range, for each pattern comprising a combination of the type of the defect, plate thickness, shape, and material.

The second flaw detection condition database DB2 has, predetermined therein, the flaw detection image used, the arrangement pattern of the image, and the contrast, according to the type of the defect, so that the defect can be detected optimally in consideration of the type of the defect, the shape, plate thickness, and material of each site.

If necessary, the contents of the flaw detection condition databases DB1, DB2 can be modified. This modification can be made by the entry of modification data by the operator via the input device 20.

Figure 9:
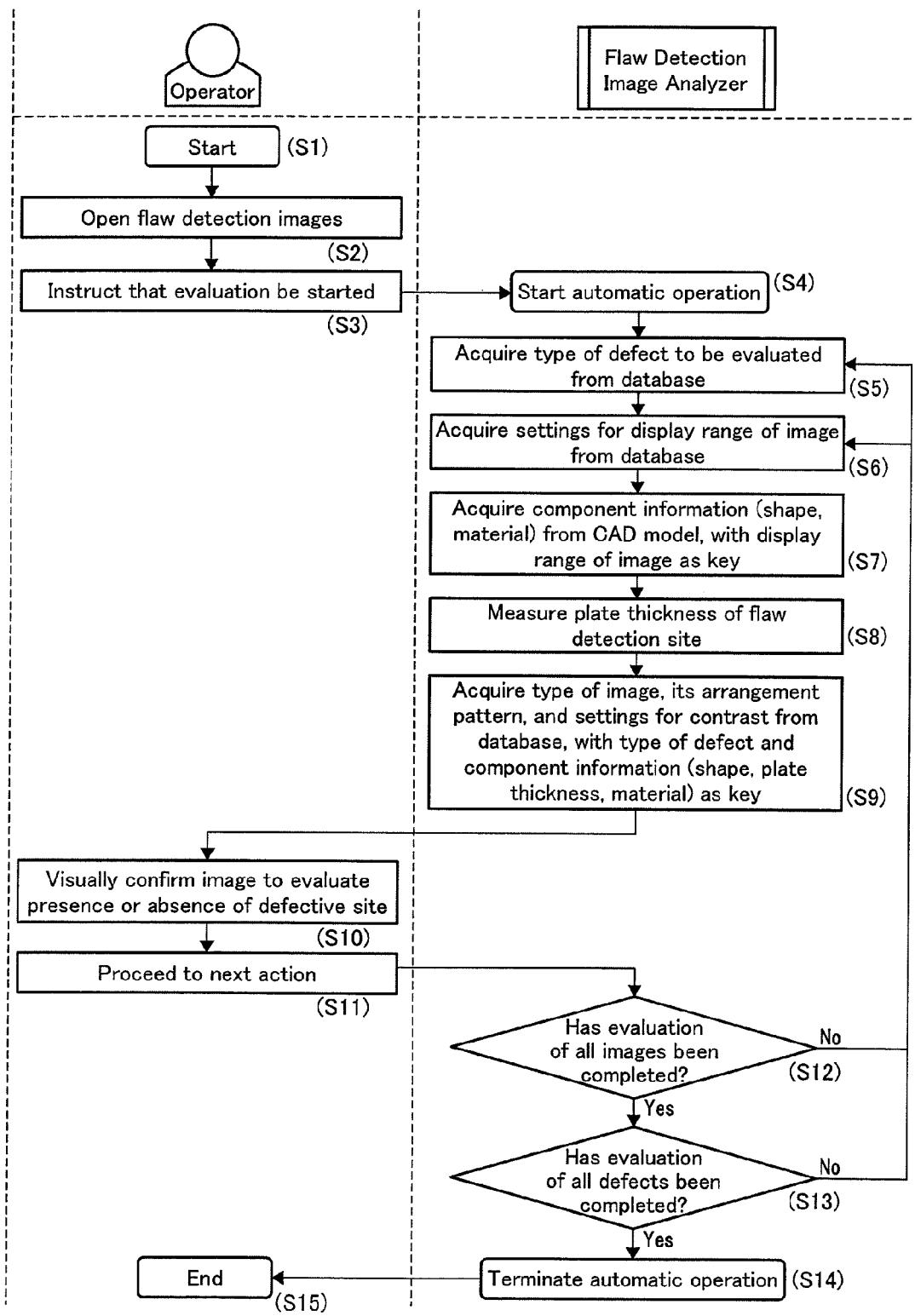
FIG. 9 is a flowchart showing the operating state of Embodiment 3.
Figure 10:
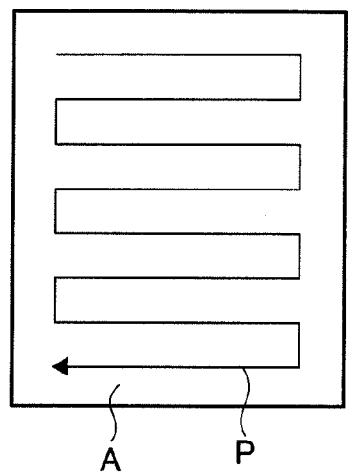
FIG. 10 is an explanation drawing showing an example of a flaw detection path.
Figure 11:
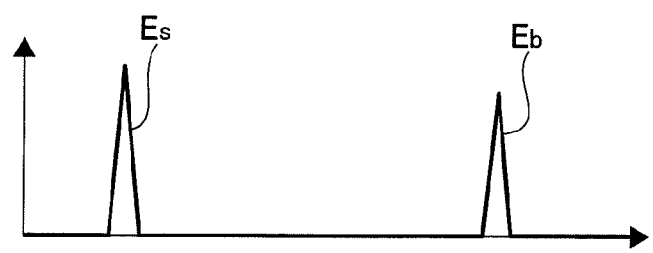
FIG. 11 is a waveform chart showing an example of a flaw detection waveform.
Figure 12:
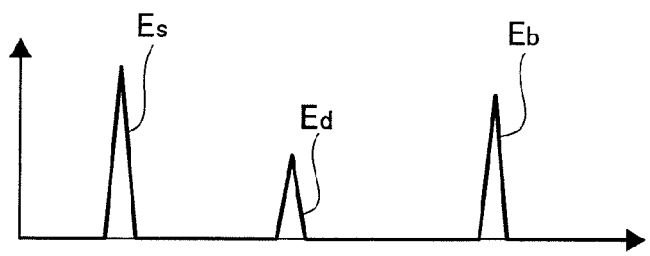
FIG. 12 is a waveform chart showing an example of a flaw detection waveform.
Figure 13:
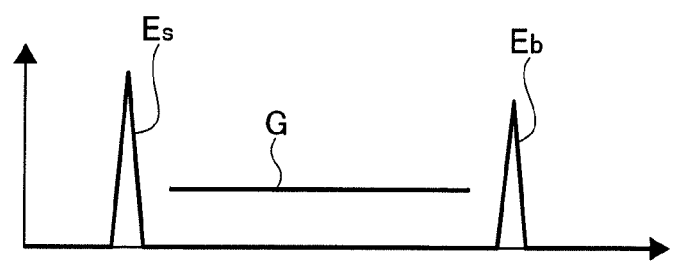
FIG. 13 is a waveform chart showing an example of the flaw detection waveform and a gate.
Figure 14:
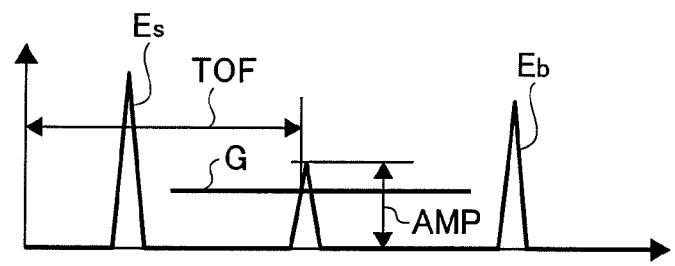
FIG. 14 is a waveform chart showing an example of the flaw detection waveform and the gate.
Figure 15:
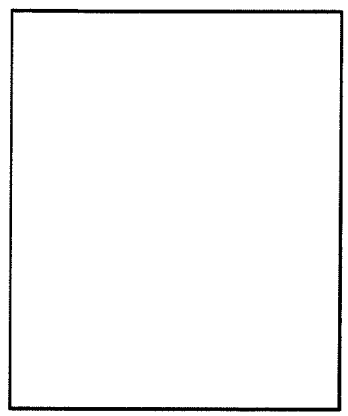
FIG. 15 is an image view showing a flaw detection image of a sound site.
Figure 16:
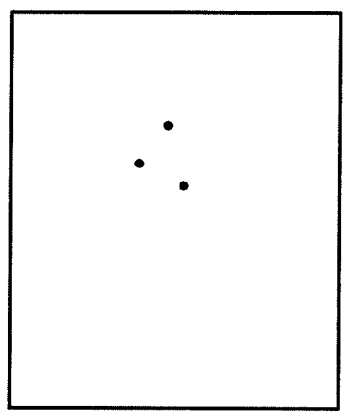
FIG. 16 is an image view showing a flaw detection image of a defective site.
Figure 17:
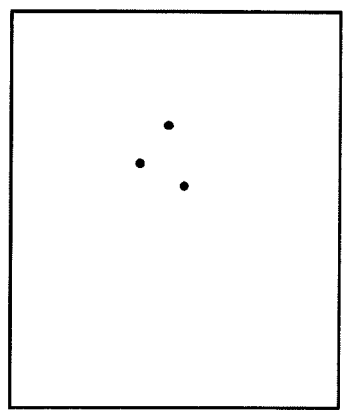
FIG. 17 is an image view showing a flaw detection image of the defective site.
Figure 18:
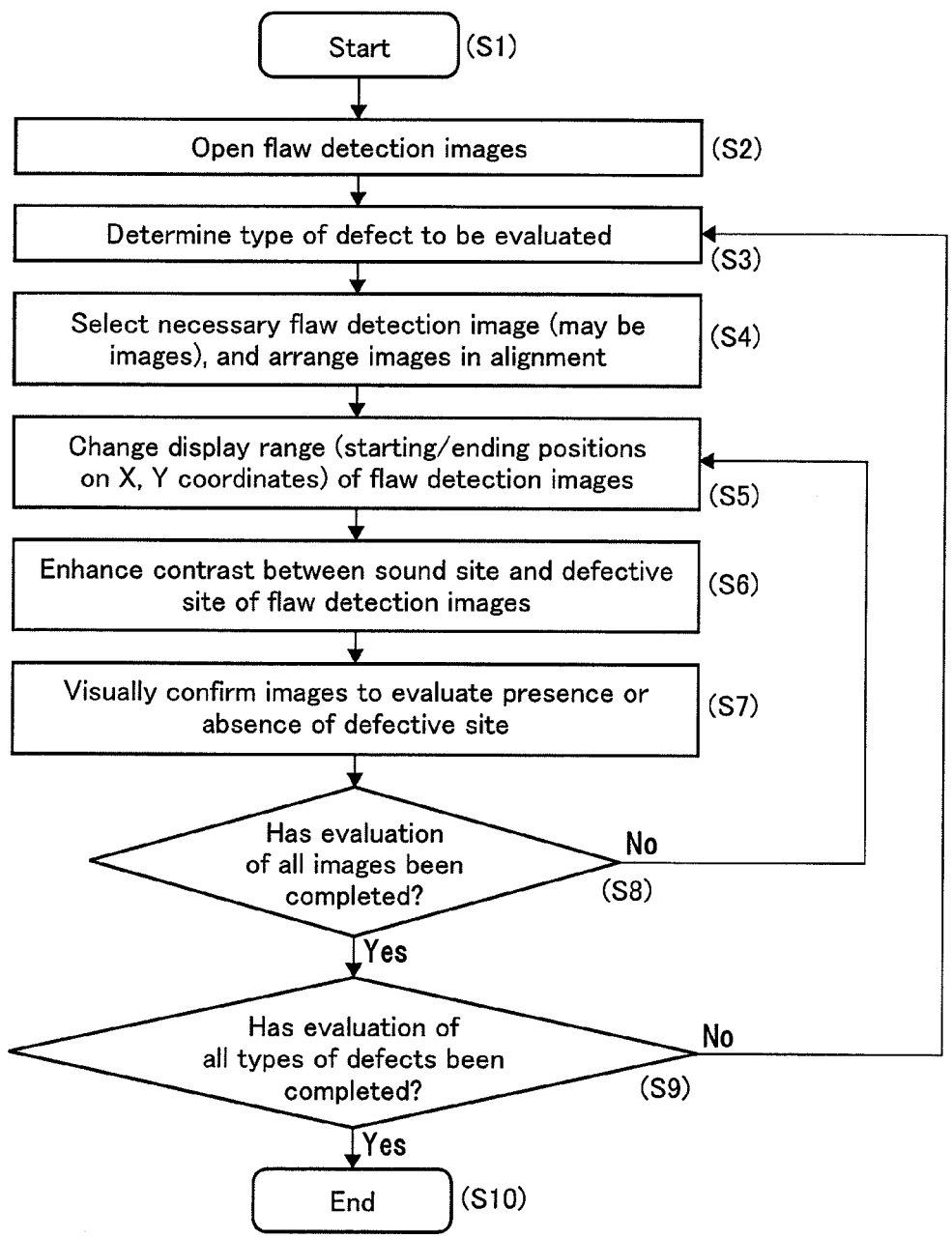
FIG. 18 is a flowchart showing the conventional procedure for analyzing a flaw detection image.
Figure 19:
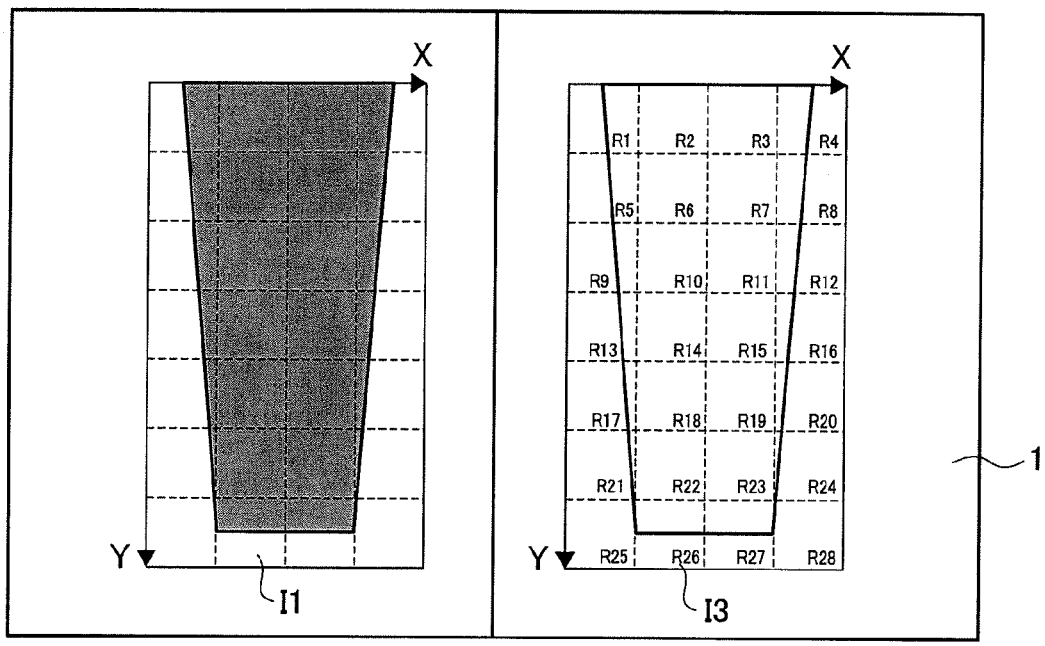
FIG. 19 is an image view showing conventional flaw detection images.
Figure 20:
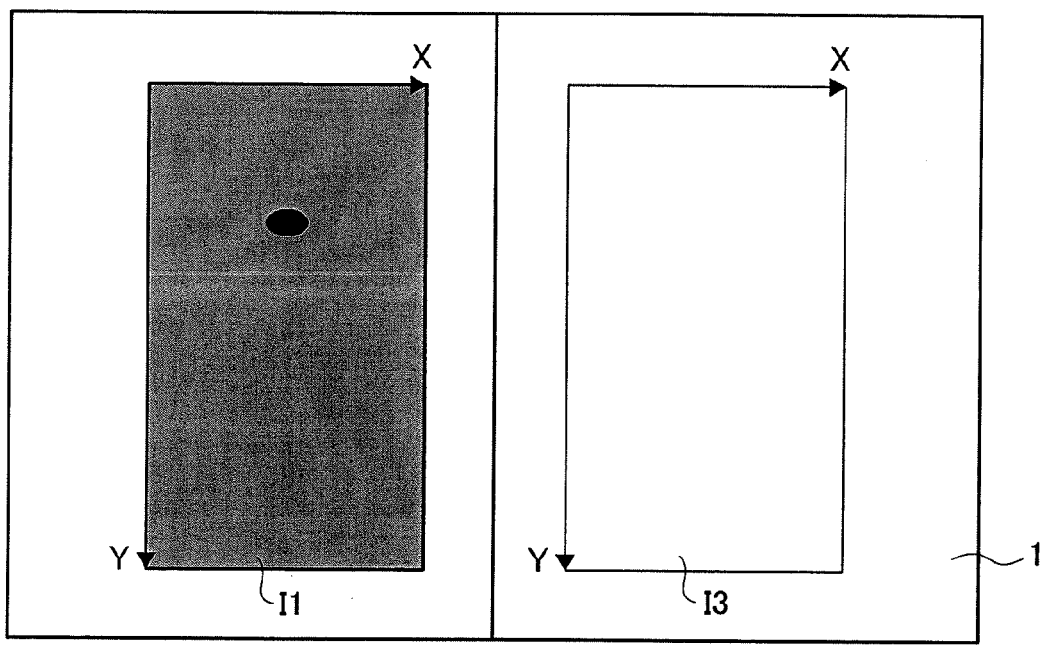
FIG. 20 is an image view showing the conventional flaw detection images.
Figure 21:
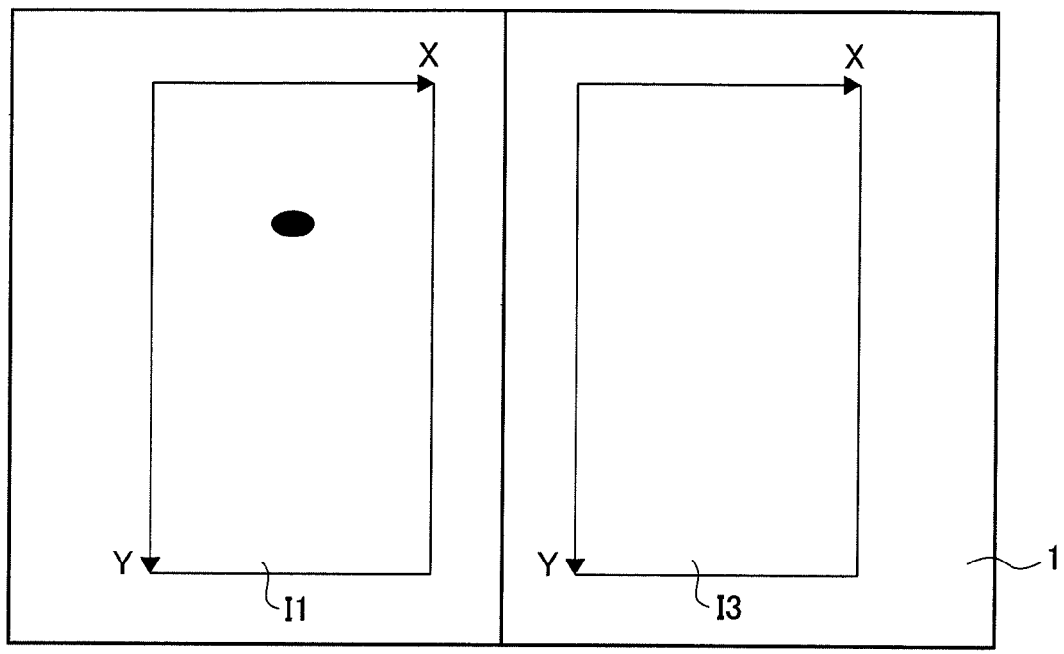
FIG. 21 is an image view showing the conventional flaw detection images.

Next, the operating state of Embodiment 3 will be described with reference to a flowchart shown in FIG. 9.

In starting inspection work (Step S1 in FIG. 9), the operator enters commands to open the flaw detection images and issue instructions to start evaluation, into the flaw detection image analyzer 10 via the input device 20 (Steps S2, S3).

Under these commands, the flaw detection image analyzer 10 captures the flaw detection image signals i1 to in from the flaw detection image signal database division 50, and stores the flaw detection image signals i1 to in into the memory within the flaw detection image analyzer 10.

An automatic operation is started by the flaw detection image analyzer 10 (Step S4).

The flaw detection image analyzer 10 refers to the first flaw detection condition database DB1 of the flaw detection condition database division 40, and carries out the inspection sequentially based on the information indicated by the inspection procedure command C.

The flaw detection image analyzer 10 first captures the inspection procedure command C1, thereby knowing that the type of the defect to be inspected for is D1 (Step S5). The flaw detection image analyzer 10 also knows the display range (the range in which the starting position X1 on the X axis is 0, the ending position X2 on the X axis is 10, the starting position Y1 on the Y axis is 0, and the ending position Y2 on the Y axis is 20) (Step S6).

Then, the flaw detection image analyzer 10 captures the shape and material of the corresponding portion of the object to be inspected (main wing), which corresponds to the display range acquired in Step S6, by reference to the CAD data stored in the three-dimensional CAD model division 60, and stores the captured CAD data (the shape is F1, and the material is M1) in a form built into the inspection procedure command C1 (Step S7).

The plate thickness of the corresponding portion of the object to be inspected (main wing) is measured by the plate thickness measuring device 70. The flaw detection image analyzer 10 captures the measured plate thickness, and stores the captured plate thickness data (the plate thickness is 10) in a form built into the inspection procedure command C1 (Step S8).

The flaw detection image analyzer 10 refers to the second flaw detection condition database DB2 of the flaw detection condition database division 40, acquiring the information set in the pattern comprising a combination of the defect type D1, plate thickness (10), shape (F1) and material (M1), namely, the information that the flaw detection image used is I1, the arrangement pattern of the flaw detection image I1 used is the maximal enlargement of a single image on the screen, the contrast minimum value of the contrast indicated values defining the contrast of the image in the display range is 20, and the contrast maximum value is 40 (Step S9).

By so referring to the inspection procedure command C1 of the first flaw detection condition database DB1, the CAD data stored in the three-dimensional CAD model division 60, the plate thickness data from the measurement by the plate thickness measuring device 70, and the second flaw detection condition database DB2, it is possible to acquire the information that the type of the defect to be inspected for is D1, the flaw detection image used in accordance with the type D1 of the defect to be inspected for is I1, the arrangement pattern of the flaw detection image I1 used is the maximal enlargement of the single image on the screen, the display range showing the range of the image region displayed among the image regions of the flaw detection image I1 used is the range in which the starting position X1 on the X axis is 0, the ending position X2 on the X axis is 10, the starting position Y1 on the Y axis is 0, and the ending position Y2 on the Y axis is 20, and the contrast minimum value of the contrast indicated values defining the contrast of the image in the display range is 20, and the contrast maximum value is 40.

Based on the so acquired information, the flaw detection image analyzer 10 maximally enlarges a single image, of the flaw detection image I1 based on the flaw detection image signal i1, in the above display range (the starting position X1 on the X axis is 0, the ending position X2 on the X axis is 10, the starting position Y1 on the Y axis is 0, and the ending position Y2 on the Y axis is 20) with the above contrast (the contrast minimum value is 20, and the contrast maximum value is 40), and displays the enlarged image on the display screen 31 of the image display device 30.

The operator visually confirms the flaw detection image displayed on the display screen 31 of the image display device 30 (the image displayed in a maximum size on the display screen 31 with the specific contrast in the display range in the specific region (magnification) of the flaw detection image I1) to evaluate whether the defect D1 is present or not (Step S10).

After visually evaluating the presence or absence of the defect D1, the operator issues a command to proceed to a next action (Step S11).

Under this command, the flaw detection image analyzer 10 captures the inspection procedure command C2, and performs the actions of Steps S5 to S9 while referring to the inspection procedure command C2, the CAD data stored in the three-dimensional CAD model division 60, the plate thickness data from the measurement by the plate thickness measuring device 70, and the second flaw detection condition database DB2. By so doing, the flaw detection image analyzer 10 maximally enlarges a single image, of the flaw detection image I1, in the display range in a specific region (the starting position X1 on the X axis is 10, the ending position X2 on the X axis is 20, the starting position Y1 on the Y axis is 0, and the ending position Y2 on the Y axis is 20) with a specific contrast (the contrast minimum value is 20, and the contrast maximum value is 40), and displays the enlarged image on the display screen 31.

The operator visually confirms the flaw detection image displayed on the display screen 31 of the image display device 30 (the image displayed in a maximum size on the display screen 31 with the specific contrast in the display range in the specific region (magnification) of the flaw detection image I1) to evaluate whether the defect D1 is present or not (Step S10).

After visually evaluating the presence or absence of the defect D1, the operator issues a command to proceed to a next action (Step S11).

Such actions are also performed under the inspection procedure commands C3, C4 . . . , which have been set consecutively, by reference to the CAD data stored in the three-dimensional CAD model division 60, the plate thickness data obtained by the measurement by the plate thickness measuring device 70, and the second flaw detection condition database DB2.

After the evaluation of the entire screen is completed in connection with the inspection for the presence or absence of the defect D1 (Step S12), the flaw detection image analyzer 10 captures the inspection procedure command C101, which is the inspection procedure command to inspect for the defect D2, in order to inspect for the presence or absence of the next defect D2.

The flaw detection image analyzer 10 first captures the inspection procedure command C101, thereby knowing that the type of the defect to be inspected for is D2 (Step S5). The flaw detection image analyzer 10 also captures the display range (the range in which the starting position X1 on the X axis is 0, the ending position X2 on the X axis is 10, the starting position Y1 on the Y axis is 0, and the ending position Y2 on the Y axis is 20) (Step S6).

Then, the flaw detection image analyzer 10 captures the shape and material of the corresponding portion of the object to be inspected (main wing), which corresponds to the display range acquired in Step S6, by reference to the CAD data stored in the three-dimensional CAD model division 60, and stores the captured CAD data (the shape is F2, and the material is M2) in a form built into the inspection procedure command C101 (Step S7).

Moreover, the plate thickness of the corresponding portion of the object to be inspected (main wing) is measured by the plate thickness measuring device 70. The flaw detection image analyzer 10 captures the measured plate thickness, and stores the captured plate thickness data (the plate thickness is 10) in a form built into the inspection procedure command C1 (Step S8).

The flaw detection image analyzer 10 refers to the second flaw detection condition database DB2 of the flaw detection condition database division 40, acquiring the information set in the pattern comprising a combination of the defect type D2, plate thickness (10), shape (F2) and material (M2), namely, the information that the flaw detection images used are I1 and I3, the arrangement pattern of the flaw detection images I1, I3 used is the placement of the two images in a laterally aligned arrangement, the contrast minimum value of the contrast indicated values defining the contrast of the image in the display range is 20 for the flaw detection image I1 and 30 for the flaw detection image I3, and the contrast maximum value is 40 for the flaw detection image I1 and 50 for the flaw detection image I3 (Step S9).

By referring, in the above-mentioned manner, to the inspection procedure command C2 of the first flaw detection condition database DB1, the CAD data stored in the three-dimensional CAD model division 60, data on the plate thickness measured by the plate thickness measuring device 70, and the second flaw detection condition database DB2, it becomes possible to acquire the information showing that the type of the defect to be inspected for is D2, the flaw detection images used in accordance with the type D2 of the defect to be inspected for are I1, I3, the arrangement pattern of the flaw detection images I1, I3 used is the placement of the two images in the laterally aligned arrangement, the display range showing the range of the image region displayed among the image regions of the flaw detection images I1, I3 used is the range in which the starting position X1 on the X axis is 0, the ending position X2 on the X axis is 10, the starting position Y1 on the Y axis is 0, and the ending position Y2 on the Y axis is 20, and the contrast minimum value of the contrast indicated values defining the contrast of the image in the display range is 20 for the flaw detection image I1 and 30 for the flaw detection image I3, and the contrast maximum value is 40 for the flaw detection image I1 and 50 for the flaw detection image I3.

Based on the so acquired information, the flaw detection image analyzer 10 displays two images in a laterally aligned arrangement on the display screen 31 of the image display device 30, the two images being images of the flaw detection images I1, I3 based on the flaw detection image signals i1, i3 and being in the above display range (the starting position X1 on the X axis is 0, the ending position X2 on the X axis is 10, the starting position Y1 on the Y axis is 0, and the ending position Y2 on the Y axis is 20) with the above contrast (the contrast minimum value is 20 for the flaw detection image I1 and 30 for the flaw detection image I3, and the contrast maximum value is 40 for the flaw detection image I1 and 50 for the flaw detection image I3).

The operator visually confirms the flaw detection images displayed on the display screen 31 of the image display device 30 (the images displayed in a laterally aligned arrangement on the display screen 31 with the specific contrast in the display range in the specific region (magnification) of the flaw detection images I1, I3) to evaluate whether the defect D2 is present or not (Step S10).

After visually evaluating the presence or absence of the defect D2, the operator issues a command to proceed to a next action (Step S11).

Under this command, the flaw detection image analyzer 10 captures the inspection procedure command C102, and performs the actions of Steps S5 to S9 while referring to the inspection procedure command C102, the CAD data stored in the three-dimensional CAD model division 60, the data on the plate thickness measured by the plate thickness measuring device 70, and the second flaw detection condition database DB2. By so doing, the flaw detection image analyzer 10 displays two images in a laterally aligned arrangement on the display screen 31, the two images being images of the flaw detection images I1, I3 and being in the display range in the specific region (the starting position X1 on the X axis is 10, the ending position X2 on the X axis is 20, the starting position Y1 on the Y axis is 0, and the ending position Y2 on the Y axis is 20) with the specific contrast (the contrast minimum value is 20 for the flaw detection image I1 and 30 for the flaw detection image I3, and the contrast maximum value is 40 for the flaw detection image I1 and 50 for the flaw detection image I3).

The operator visually confirms the flaw detection images displayed on the display screen 31 of the image display device 30 (the images displayed in a laterally aligned arrangement on the display screen 31 with the specific contrast in the display range in the specific region (magnification) of the flaw detection images I1, I3) to evaluate whether the defect D2 is present or not (Step S10).

After visually evaluating the presence or absence of the defect D2, the operator issues a command to proceed to a next action (Step S11).

Such actions are also performed under the inspection procedure commands C103 . . . , which have been set consecutively, by reference to the CAD data stored in the three-dimensional CAD model division 60, the plate thickness data from the measurement by the plate thickness measuring device 70, and the second flaw detection condition database DB2.

After the evaluation of the entire screen is completed in connection with the inspection for the presence or absence of the defect D2 (Step S12), the flaw detection image analyzer 10 captures the inspection procedure command CN, which is the inspection procedure command to inspect for the defect D3, in order to inspect for the presence or absence of the next defect D3. The flaw detection image analyzer 10 performs the same processings as mentioned above, and displays the images. The operator visually confirms the displayed images, and can thereby evaluate whether the defect is present or not.

After the inspection procedure command C is executed up to the end and the evaluation of all the defects is completed (Step S13), the flaw detection image analyzer 10 terminates the automatic operation (Step S14), and then the analysis work on the flaw detection images (defect detection work) is completed (Step S15).

It is possible to make settings such that when the operator has visually confirmed the defects, the sites and types of the defects are stored into the flaw detection image analyzer 10 and, after completion of work on the defect inspection, the stored defective sites are displayed on the display screen 31 by the type of the defect.

In the above-described manner, the flaw detection image analyzer 10 performs the automatic operation, whereby the images of the optimal type in the optimal arrangement state, in the optimal display range (magnification) with the optimal contrast, are sequentially displayed on the display screen 31 of the image display device 30 in accordance with the type of each defect. Thus, the operator can conduct the inspection for the defect while looking at the display screen, without the need to select the image or to carry out an operation for changing the display position, display magnification, or the like.

Hence, the inspection for the defect can be easily performed in a short time, and even an inspector with little experience can conduct the defect inspection accurately without an omission of inspection.

Based on the type of the defect, plate thickness, shape, and material, moreover, the flaw detection image used, and the arrangement pattern and contrast of the image are acquired from the second flaw detection condition database DB2. This obviates the necessity of registering the flaw detection image used, and the arrangement pattern and contrast of the image, individually on all the inspection procedure commands. Thus, it becomes easy to create a flaw detection condition database as a whole.

Furthermore, the plate thickness of the site to be inspected is actually measured by the plate thickness measuring device 70, so that the plate thickness data need not be stored in the database. Even if variations in the plate thickness are present in each object to be inspected, a flaw detection test can be conducted using the correct setting conditions (plate thickness dimensions).

INDUSTRIAL APPLICABILITY

The present invention can be applied not only in detecting the defect of a wing of an aircraft, but also in detecting a defect, by ultrasonic flaw defection, in various products to be inspected, in which a defect can be detected by ultrasonic flaw detection.

DESCRIPTION OF THE NUMERALS

10 Flaw detection image analyzer
20 Input device
30 Image display device
31 Display screen
40 Flaw detection condition database division
50 Flaw detection image signal database division
60 Three-dimensional CAD model division
70 Plate thickness measuring device

The invention claimed is:

1. An analytical apparatus for an ultrasonic flaw detection image, comprising:
 a flaw detection image signal database division storing a plurality of flaw detection image signals obtained by signal transformation of an identical flaw detection waveform signal by a plurality of different signal transformation techniques;
 a flaw detection condition database division storing a flaw detection condition database constructed from many inspection procedure commands arranged in order of execution, the inspection procedure commands having, as information, a type of a defect to be inspected for, a flaw detection image used in accordance with the type of the defect to be inspected for, an arrangement pattern of the flaw detection image used, a display range showing a range of an image region displayed among image regions of the flaw detection image used, and contrast indicated values defining a contrast of an image in the display range; and
 a flaw detection image analyzer,
 wherein the flaw detection image analyzer
 captures the inspection procedure commands of the flaw detection condition database sequentially based on input commands from an outside,
 whenever the inspection procedure command is captured, captures from the flaw detection image signal database division the flaw detection image signal corresponding to the flaw detection image indicated by the captured inspection procedure command, and
 allows a display device to display the flaw detection image based on the flaw detection image signal in the arrangement pattern of the image indicated by the inspection procedure command, in the display range indicated by the inspection procedure command, and with the contrast indicated by the inspection procedure command.

* * * * *